US011358352B2

(12) United States Patent
Kitagawa et al.

(10) Patent No.: US 11,358,352 B2
(45) Date of Patent: Jun. 14, 2022

(54) METHOD FOR PRODUCING MEDICAL DEVICE

(71) Applicant: Toray Industries, Inc., Tokyo (JP)

(72) Inventors: Rumiko Kitagawa, Otsu (JP); Masataka Nakamura, Otsu (JP)

(73) Assignee: TORAY INDUSTRIES, INC., Tokyo (JP)

(*) Notice: Subject to any disclaimer, the term of this patent is extended or adjusted under 35 U.S.C. 154(b) by 287 days.

(21) Appl. No.: 16/608,999

(22) PCT Filed: Apr. 26, 2018

(86) PCT No.: PCT/JP2018/017039
§ 371 (c)(1),
(2) Date: Oct. 28, 2019

(87) PCT Pub. No.: WO2018/207644
PCT Pub. Date: Nov. 15, 2018

(65) Prior Publication Data
US 2020/0139653 A1    May 7, 2020

(30) Foreign Application Priority Data
May 11, 2017   (JP) .............................. JP2017-094412

(51) Int. Cl.
B29D 11/00    (2006.01)
G02B 1/04     (2006.01)

(52) U.S. Cl.
CPC ........ B29D 11/00038 (2013.01); G02B 1/043 (2013.01); B29K 2995/0092 (2013.01)

(58) Field of Classification Search
CPC .............. B29D 11/00038; G02B 1/043; B29K 2995/0092
See application file for complete search history.

(56) References Cited

U.S. PATENT DOCUMENTS

| 4,168,112 A | 9/1979 | Ellis et al. |
| 4,321,261 A | 3/1982 | Ellis et al. |
| 2003/0052424 A1 | 3/2003 | Turner et al. |
| 2008/0100796 A1 | 5/2008 | Pruitt et al. |
| 2009/0173045 A1 | 7/2009 | Lai et al. |
| 2012/0026457 A1 | 2/2012 | Qiu et al. |
| 2013/0118127 A1 | 5/2013 | Kolluru et al. |
| 2019/0015542 A1 | 1/2019 | Kitagawa et al. |
| 2019/0022282 A1 | 1/2019 | Kitagawa et al. |

FOREIGN PATENT DOCUMENTS

| EP | 3395376 A1 | 10/2018 |
| JP | 54116947 A | 9/1979 |
| JP | 63246718 A | 10/1988 |
| JP | 2002047365 A | 2/2002 |
| JP | 2005520703 A | 7/2005 |
| JP | 2010508563 A | 3/2010 |
| JP | 2011512546 A | 4/2011 |
| JP | 2013533517 A | 8/2013 |
| JP | 2014533381 A | 12/2014 |
| JP | 201723374 A | 2/2017 |
| WO | 2013024800 A1 | 2/2013 |

OTHER PUBLICATIONS

International Search Report and Written Opinion for International Application No. PCT/JP2018/017039, dated Jul. 24, 2018. 7 Pages.
Extended European Search Report for European Application No. 18 798 979.3, dated Mar. 1, 2021, 7 pages.

Primary Examiner — Mathieu D Vargot
(74) Attorney, Agent, or Firm — RatnerPrestia

(57) ABSTRACT

The present invention provides a method for producing a medical device, which includes a step of disposing a solution containing a hydrophilic polymer having a hydroxyl group and an amide group and a substrate on or in a support, and heating the solution and the substrate through the support, wherein a pH of the solution before starting the heating step is in a range of 2.0 or higher and 6.0 or lower, and a pH of the solution after completion of the heating step is in a range of 2.0 or higher and 6.0 or lower. The present invention provides a method for simply producing a medical device. More particularly, the present invention provides a method for simply producing a medical device whose surface is hydrophilized.

11 Claims, No Drawings

METHOD FOR PRODUCING MEDICAL DEVICE

CROSS REFERENCE TO RELATED APPLICATIONS

This is the U.S. National Phase application of PCT/JP2018/017039, filed Apr. 26, 2018, which claims priority to Japanese Patent Application No. 2017-094412, filed May 11, 2017, the disclosures of each of these applications being incorporated herein by reference in their entireties for all purposes.

FIELD OF THE INVENTION

The present invention relates to a method for producing a medical device. More particularly, the present invention relates to a method for producing a medical device having a hydrophilic surface.

BACKGROUND OF THE INVENTION

There have hitherto been used devices using soft materials made of resins such as a silicone rubber and hydrogel and devices using hard materials such as metal and glass in various fields. Applications of devices using soft materials include medical devices for introduction into a living body and for covering a surface of a living body, biotechnology devices such as cell culture sheets and scaffold materials for tissue regeneration, and cosmetic devices such as facial packs. Applications of devices using hard materials include electric appliances such as personal computers, mobile phones, displays, etc., ampules for use in injections, and use as diagnostic and analysis tools such as capillaries, biosensing chips, and the like.

When various devices are introduced into a living body as a medical device or attached to a surface of a living body, in order to make it easy for adaptation to the living body, it becomes important to perform surface modification for improving biocompatibility such as hydrophilicity and lubricity. If it is possible to impart better properties such as hydrophilicity, lubricity, and biocompatibility than before surface modification to medical devices, users (patients, etc.) can expect an improvement in tactile sensation, reduction of discomfort, and the like.

Various methods have been known as a method for modification of a surface of a substrate of medical devices.

In the prior art, since it was difficult to impart sufficient hydrophilicity in the case of one polymer material, there has been known a method of laminating by forming a layer of each of two or more polymer materials one by one through coating (see, for example, Patent Literature 1). Of these, a method of laminating by forming a layer of each of two or more polymer materials one by one on a layer having a charge opposite to that of the lower layer to coat layers having alternately different charges is called a layer by layer method (LbL method) or the like. In such coating obtained by the LbL method, it is considered that each layer of a substrate and a polymer material is bonded to other layer by the electrostatic interaction.

To improve cost efficiency, there has recently been disclosed, as an improved method of the LbL method, a method in which a polyionic substance and a hydrolysate substance during autoclaving are used and the polyionic substance is adsorbed onto a surface of a silicone hydrogel by a single heat treatment and, at the same time, the surface of the silicone hydrogel is hydrophilized (see Patent Literature 2).

There is disclosed a method in which two hydrophilic polymers are crosslinked on a surface of a silicone hydrogel by a single heat treatment (see Patent Literature 3).

There is also disclosed a surface coating of a contact lens with an ionic polymer (see Patent Literatures 4 to 6).

There is also disclosed a coating method of an article due to mold transfer in which at least one coating agent is coated on a mold surface and an article-forming material is cured in the mold to form an article (see Patent Literature 7).

PATENT LITERATURE

[Patent Literature 1] WO 2013/024800 A
[Patent Literature 2] JP 2010-508563 W
[Patent Literature 3] JP 2014-533381 W
[Patent Literature 4] JP 54-116947 A
[Patent Literature 5] JP 63-246718 A
[Patent Literature 6] JP 2002-047365 A
[Patent Literature 7] JP 2005-520703 W

SUMMARY OF THE INVENTION

However, in conventional LbL coating as mentioned in Patent Literatures 1 and 2, it is usually performed to laminate multilayers of about 3 to 20 layers. Lamination of multilayers leads to an increase in production processes, and thus the production cost may increase.

In improved LbL coating as mentioned in Patent Literature 2, applicable substrate is limited to a hydrous hydrogel.

With respect to the method in which two hydrophilic polymers are crosslinked by a single heat treatment as mentioned in Patent Literature 3, applicable substrate is also limited to a hydrous hydrogel. In the method as mentioned in Patent Literature 3, there is a need for a process in which a carboxyl group-containing polymer is crosslinked to a silicone hydrogel surface before a heat treatment. Via a covalent bond between an epoxide group of a crosslinkable hydrophilic polymer material and a carboxyl group crosslinked on the silicone hydrogel surface, a hydrophilic polymer is crosslinked on a lens surface. This crosslinking is performed in an aqueous solution. Since there is a need for such a complicated process, the production cost may increase.

In surface coating of a contact lens with an ionic polymer as mentioned in Patent Literatures 4 to 6, performances such as hydrophilicity of the surface were still insufficient.

In the coating method as mentioned in Patent Literature 7, the mold used to apply the coating agent includes the inside of the mold and a space between both molds and an external non-molded surface is not included, so that it was difficult to reuse the mold using the non-molded surface. Applicable substrate was limited to a hydrous hydrogel and a silicone hydrogel.

The present invention has been made in view of aforementioned problems of prior art. Thus, it is an object of the present invention to provide a method for simply producing a medical device. More particularly, it is an object of the present invention to provide a method for simply producing a medical device whose surface is hydrophilized.

To achieve the above object, the present invention is directed to the following method.

The present invention according to exemplary embodiments is directed to a method for producing a medical device, which includes a step of disposing a solution containing a hydrophilic polymer having a hydroxyl group and an amide group and a substrate on or in a support, and heating the solution and the substrate through the support, wherein a pH of the solution before starting the heating step is in a range of 2.0 or higher and 6.0 or lower, and a pH of the solution after completion of the heating step is in a range of 2.0 or higher and 6.0 or lower.

According to the present invention, unlike the prior art, it is possible to obtain a medical device imparted with hydrophilicity by a simple process since a substrate surface is hydrophilized by a simple method. Applicable substrate is not limited to a hydrous hydrogel and a silicone hydrogel.

DETAILED DESCRIPTION OF EMBODIMENTS OF THE INVENTION

The present invention according to exemplary embodiments is directed to a method for producing a medical device, which includes a step of disposing a solution containing a hydrophilic polymer having a hydroxyl group and an amide group and a substrate on or in a support, and heating the solution and the substrate through the support, wherein a pH of the solution before starting the heating step is in a range of 2.0 or higher and 6.0 or lower, and a pH of the solution after completion of the heating step is in a range of 2.0 or higher and 6.0 or lower.

In an embodiment of the present invention, it is possible to use, as a substrate, both a hydrous substrate and a non-hydrous substrate.

Specifically, the material of the hydrous substrate includes a hydrogel or the like. Examples of the material of the non-hydrous substrate include an acrylic resin such as polymethyl methacrylate, a silicone substrate having a siloxane bond, metal such as aluminum, and glass.

The present invention according to exemplary embodiments is also applicable to an ordinary hydrogel containing no silicone and a hydrogel containing silicone (silicone hydrogel) with respect to a material of a hydrous substrate. It is possible to use particularly suitably for the silicone hydrogel since surface physical properties can be significantly improved.

The medical device is obtained by subjecting the substrate to the heating step and, if necessary, the production process such as a washing step. Specific examples of the medical device will be mentioned later.

According to an embodiment of the present invention, it is possible to impart moderate hydrophilicity and lubricity to a surface of the medical device even if the substrate may be hydrous or non-hydrous. Therefore, the moisture content of substrate may be 0 to 99% by mass. The moisture content of the substrate is preferably 0.0001% by mass or more, and most preferably 0.001% by mass or more, since the effect of imparting moderate hydrophilicity and lubricity to the medical device surface is further enhanced. The moisture content of the substrate is preferably 60% by mass or less, more preferably 50% by mass or less, and still more preferably 40% by mass or less.

Examples of the form of the substrate include a tube shape or a form having a space therein, a sheet shape, a film shape, a storage container shape, a lens shape and the like.

According to an embodiment of the present invention, it is preferable that a hydrophilic polymer layer is formed on at least a part of a substrate surface. The hydrophilicity is imparted to a surface of the resulting medical device by the existence of the hydrophilic polymer layer on the substrate surface. The hydrophilic polymer layer existing on the substrate surface is a layer in which a hydrophilic polymer having a hydroxyl group and an amide group is formed as a layer on the substrate surface by the heating step. A part of the hydrophilic polymer layer may enter into the inside of the substrate. The material constituting the polymer layer is usually a material different from that of the substrate. However, as long as a predetermined effect can be obtained, the material may be the same material as that constituting the substrate. As long as the development of the hydrophilicity is not impaired, additives other than the hydrophilic polymer may be included in the hydrophilic polymer layer.

Here, the hydrophilic polymer is a polymer which is soluble in 100 parts by mass of water at room temperature (20 to 23° C.) in the amount of 0.0001 part by mass or more, preferably 0.01 part by mass or more, more preferably 0.1 part by mass or more, and particularly preferably 1 part by mass or more, based on 100 parts by mass of water.

A hydrophilic polymer having a hydroxyl group and an amide group is used as the hydrophilic polymer. The hydrophilic polymer having a hydroxyl group is preferable because it can form a surface excellent in not only water wettability but also antifouling properties against body fluid, and the like. The hydrophilic polymer having a hydroxyl group as used herein is preferably a polymer having an acidic hydroxyl group. Specifically, a polymer having a group selected from a carboxyl group and a sulfonic acid group is preferable, and a polymer having a carboxyl group is most preferable. The carboxyl group or the sulfonic acid group may be in the form of a salt.

Examples of the hydrophilic polymer having a hydroxyl group include polymethacrylic acid, polyacrylic acid, poly(vinylbenzoic acid), poly(thiophene-3-acetic acid), poly(4-styrenesulfonic acid), polyvinylsulfonic acid, poly(2-acrylamido-2-methylpropanesulfonic acid), and salts thereof. Those mentioned above are examples of a homopolymer, and it is also possible to suitably use a copolymer of hydrophilic monomers constituting the hydrophilic polymer, or a copolymer of the hydrophilic monomer and the other monomer.

When the hydrophilic polymer having a hydroxyl group is a copolymer, the hydrophilic monomer constituting the copolymer is preferably a monomer having a group selected from an allyl group, a vinyl group, and a (meth)acryloyl group in view of high polymerizability. The monomer having a (meth)acryloyl group is most preferable. Suitable examples of such monomer include (meth)acrylic acid, vinylbenzoic acid, styrenesulfonic acid, vinylsulfonic acid, 2-acrylamido-2-methylpropanesulfonic acid, and salts thereof. Of these, a monomer selected from (meth)acrylic acid, 2-acrylamido-2-methylpropanesulfonic acid, and salts thereof is more preferable, and a monomer selected from (meth)acrylic acid and salts thereof is most preferable.

The hydrophilic polymer has an amide group, in addition to the hydroxyl group, thus enabling formation of a surface having not only water wettability but also lubricity. The hydrophilic polymer having a hydroxyl group and an amide group develops moderate viscosity when dissolved in water, thus enabling formation of a surface having not only water wettability but also lubricity.

Examples of the acidic hydrophilic polymer having a hydroxyl group and an amide group include polyamides having a carboxyl group, a copolymer of a monomer having a hydroxyl group and a monomer having an amide group, and the like.

Suitable examples of the polyamides having a carboxyl group include polyamino acids such as polyaspartic acid and polyglutamic acid, and polypeptides.

It is possible to suitably use, as the monomer having a hydroxyl group, a monomer selected from methacrylic acid, acrylic acid, vinylbenzoic acid, thiophene-3-acetic acid, 4-styrenesulfonic acid, vinylsulfonic acid, 2-acrylamido-2-methylpropanesulfonic acid, and salts thereof.

In view of ease of polymerization, the monomer having an amide group is preferably a monomer selected from a monomer having a (meth)acrylamide group and N-vinylcarboxylic acid amide (including cyclic one). Suitable Examples of such monomer include N-vinylpyrrolidone, N-vinylcaprolactam, N-vinylacetamide, N-methyl-N-vinylacetamide, N-vinylformamide, N,N-dimethylacrylamide, N,N-diethylacrylamide, N-isopropylacrylamide, N-(2-hydroxyethyl)acrylamide, acryloyl morpholine, and acrylamide. Of these, N-vinylpyrrolidone and N,N-dimethylacrylamide are preferable in view of the lubricity, and N,N-dimethylacrylamide is most preferable.

When the hydrophilic polymer having an amide group in addition to the hydroxyl group is a copolymer, preferred specific examples are a (meth)acrylic acid/N-vinylpyrrolidone copolymer, a (meth)acrylic acid/N,N-dimethylacrylamide copolymer, a 2-acrylamido-2-methylpropanesulfonic acid/N-vinylpyrrolidone copolymer, and a 2-acrylamido-2-methylpropanesulfonic acid/N,N-dimethylacrylamide copolymer. A (meth)acrylic acid/N,N-dimethylacrylamide copolymer is most preferable.

When using a copolymer of a monomer having a hydroxyl group and a monomer having an amide group, the copolymerization ratio thereof is preferably in a range of 1/99 to 99/1 in terms of [mass of monomer having a hydroxyl group]/[mass of monomer having an amide group]. The copolymerization ratio of the monomer having a hydroxyl group is more preferably 2% by mass or more, still more preferably 5% by mass or more, and yet more preferably 10% by mass or more. The copolymerization ratio of the monomer having a hydroxyl group is more preferably 90% by mass or less, still more preferably 80% by mass or less, and yet more preferably 70% by mass or less. The copolymerization ratio of the monomer having an amide group is more preferably 10% by mass or more, still more preferably 20% by mass or more, and yet more preferably 30% by mass or more. The copolymerization ratio of the monomer having an amide group is more preferably 98% by mass or less, still more preferably 95% by mass or less, and yet more preferably 90% by mass or less. If the copolymerization ratio of the monomer having a hydroxyl group to the monomer having an amide group is within the above range, functions such as lubricity and antifouling properties against body fluid are easily developed.

It is also possible to further copolymerize the monomer having a hydroxyl group and the monomer having an amide group with a different monomer having a hydroxyl group or an amide group, and one or more monomers having neither hydroxyl group nor amide group.

Suitable examples of the monomer other than the above monomers include hydroxyethyl (meth)acrylate, hydroxypropyl (meth)acrylate, hydroxybutyl (meth)acrylate, hydroxyethyl(meth)acrylamide, glycerol (meth)acrylate, caprolactone-modified 2-hydroxyethyl (meth)acrylate, N-(4-hydroxyphenyl)maleimide, hydroxystyrene, and vinyl alcohol (carboxylic acid vinyl ester as a precursor). Of these, in view of ease of polymerization, a monomer having a (meth)acryloyl group is preferable and a (meth)acrylic acid ester monomer is more preferable. From the viewpoint of improving antifouling properties against body fluid, hydroxyethyl (meth)acrylate, hydroxypropyl (meth)acrylate, and glycerol (meth)acrylate are preferable, and hydroxyethyl (meth)acrylate is particularly preferable. It is also possible to use a monomer having functions such as hydrophilicity, antibacterial properties, and antifouling properties.

In addition to the hydrophilic polymer having a hydroxyl group and an amide group, one or more other hydrophilic polymers may be included in the hydrophilic polymer layer. Since the production method may be complicated, the hydrophilic polymer layer is preferably made of only one hydrophilic polymer having a hydroxyl group and an amide group.

Here, one polymer means a polymer or a polymer group (including isomers, complexes, etc.) produced by one synthesis reaction. When a copolymerized polymer is obtained by using plural monomers, a polymer synthesized by changing a compounding ratio is not said to be one polymer even though the constituent monomer species are the same.

The expression that the hydrophilic polymer layer is made of only one hydrophilic polymer having a hydroxyl group and an amide group means that the hydrophilic polymer layer does not contain any polymer other than the hydrophilic polymer having a hydroxyl group and an amide group, or even if it contains a polymer other than that, it means that the content of the polymer other than that is 3 parts by mass or less based on 100 parts by mass of the hydrophilic polymer having a hydroxyl group and an amide group. The content of the polymer other than that is more preferably 0.1 part by mass or less, and still more preferably 0.0001 part by mass or less. Even if the hydrophilic polymer contains a basic polymer as the hydrophilic polymer having a hydroxyl group and an amide group, when the content is within the above range, it is possible to suppress the occurrence of a problem with transparency. In the prior art, an acidic polymer and a basic polymer were used in combination to laminate a hydrophilic polymer on a surface of a substrate utilizing the electrostatic adsorption effect. However, according to the present invention, a hydrophilic polymer layer made of only one polymer can be formed on a surface of the substrate.

In a method for producing a medical device according to embodiments of the present invention, a solution containing a hydrophilic, polymer having a hydroxyl group and an amide group and a substrate are disposed on or in a support, and the hydrophilic polymer is fixed on at least a part of a surface of the substrate by a step of heating the solution and the substrate through the support. Here, fixing means that the hydrophilic polymer is firmly fixed on a surface of the substrate. The hydrophilic polymer may be bonded to the substrate through a covalent bond, or rather, the hydrophilic polymer preferably has no covalent bond with the substrate since it becomes possible to produce by a simple process. Here, fixing without having a covalent bond means fixing through a hydrogen bond, an ionic bond, a van der Waals bond, a hydrophobic bond, complex formation or the like. Since a covalent bond is easily formed when the hydrophilic polymer has a chemically reactive group, the hydrophilic polymer preferably has no chemically reactive group. Specific examples of the chemically reactive group include an azetidinium group, an epoxy group, an isocyanate group, an aziridine group, an azlactone group, and combinations thereof.

Depending on the application, the hydrophilic polymer layer preferably exists on the entire surface of one surface of the substrate surface in the medical device obtained by the production method of the present invention. In the case of a two-dimensional shape in which the substrate has no thickness or, if any, thickness can be neglected, the hydrophilic polymer layer preferably exists on the entire surface of one surface of the substrate surface. More preferably, the hydrophilic polymer layer exits on the entire surface of the substrate.

The thickness of the hydrophilic polymer layer is preferably 1 nm or more and less than 100 nm when observing a cross section of the device in a frozen state (hereinafter referred to as a frozen state) in a hydrous state using a scanning transmission electron microscope since it is easy to exhibit functions such as water wettability and lubricity. The thickness is more preferably 5 nm or more, still more preferably 10 nm or more, and most preferably 15 nm or more. The thickness is more preferably 90 nm or less, still more preferably 80 nm or less, and most preferably 70 nm or less. It is possible to measure the thickness of the hydrophilic polymer layer in a frozen state by scanning transmission electron microscope observation using a cryotransfer holder. When the thickness of the polymer layer in a frozen state is 100 nm or more, for example, in the case of using for a medical device such as an ophthalmic lens, refraction of light for focusing on the retina is disturbed and poor visibility easily occur, unfavorably.

The thickness of the hydrophilic polymer layer in a dry state is preferably 1 to 100 nm, since functions such as water wettability and lubricity are easily exhibited. The thickness is more preferably 10 nm or more, and still more preferably 20 nm or more. The thickness is more preferably 90 nm or less, still more preferably 80 nm or less, and most preferably 70 nm or less. When the thickness of the hydrophilic polymer layer is 100 nm or less, the hydrophilic polymer layer is excellent in water wettability and lubricity and, for example, in the case of using for a medical device such as an ophthalmic lens, refraction of light for focusing on the retina is not disturbed and poor visibility becomes hardly occurs.

The hydrophilic polymer layer is preferably in a state of being separated into two or more layers or two or more phases.

Here, the state where the hydrophilic polymer layer is separated into two or more layers means a state where a multilayer structure of two or more layers is observed in the hydrophilic polymer layer when a cross section of the medical device is observed using a transmission electron microscope. If it is difficult to judge separation of layers only by observation with a transmission electron microscope, separation of layers is judged by analyzing elements and compositions of a cross section of the medical device using means capable of performing elemental analysis and composition analysis, such as scanning transmission electron microscopy and electron energy-loss spectroscopy, energy dispersive X-ray spectroscopy, or time-of-flight secondary ion mass spectrometry. The state where the hydrophilic polymer layer is separated into two or more phases means a state where a state of phase separation into two or more phases in the hydrophilic polymer layer is observed when a cross section of the medical device is observed using a transmission electron microscope. The case where it is difficult to judge separation of phases only by observation with a transmission electron microscope is the same as mentioned above.

Two or more polymers have conventionally been required so as to form a polymer layer of two or more layers or two or more layers on a substrate surface. However, it has been found in an embodiment of the present invention that it is possible to form a hydrophilic polymer layer separated into two or more layers or two or more phases on a Substrate surface even if only one polymer exists.

When the hydrophilic polymer layer has a multilayer structure of two or more layers, the thickness of the hydrophilic polymer layer sufficiently increases, leading to further improvement in satisfactory water wettability and lubricity. In a state where the hydrophilic polymer layer is separated into two or more phases, it becomes easy to distinguish from foreign matters such as dust when a cross section of the medical device is observed using a transmission electron microscope. Therefore, it is easy to confirm formation of the polymer layer on the substrate surface and is efficient for quality inspection.

In the hydrophilic polymer layer, at least a part of the hydrophilic polymer layer preferably exists in a state of being mixed with the substrate. The state where the hydrophilic polymer layer is mixed with the substrate is determined by the fact that elements derived from the substrate are detected in at least a part of the hydrophilic polymer layer when a cross section of the medical device is observed using observation means capable of performing elemental analysis or composition analysis, such as scanning transmission electron microscopy, electron energy-loss spectroscopy, energy dispersive X-ray spectroscopy, or time-of-flight secondary ion mass spectrometry. By mixing the hydrophilic polymer layer with the substrate, the hydrophilic polymer can be firmly fixed to the substrate.

When at least a part of the hydrophilic polymer layer exists in a state of being mixed with the substrate, it is preferred to observe a two-layer structure of a "layer in which at least a part of a hydrophilic polymer layer is mixed with a substrate" (hereinafter referred to as a "mixed layer") and a "layer made of a hydrophilic polymer (hereinafter referred to as a single layer). The thickness of the mixed layer is preferably 3% or more, more preferably 5% or more, and still more preferably 10% or more, based on the total thickness of the mixed layer and the single layer. The thickness of the mixed layer is preferably 98% or less, more preferably 95% or less, still more preferably 90% or less, and most preferably 80% or less, based on the total thickness of the mixed layer and the single layer. Too small thickness ratio of the mixed layer leads to insufficient mixing of the hydrophilic polymer with the substrate, unfavorably. Too large thickness ratio of the mixed layer may lead to insufficient development of properties of the hydrophilic polymer, unfavorably.

From the viewpoint of excellent transparency of the medical device, the number of layers or phases is preferably 2 to 3, and more preferably 2. If the medical device has high transparency, for example, when the medical device is used as a skin material, it is easy to visually observe the state of the skin without peeling the medical device from the skin. If the medical device has high transparency, it can be used as an ophthalmic lens or the like.

In a preferred embodiment of the present invention, the medical device of the present invention may be in the form of a tube. Examples of tubular devices include an infusion tube, a gas delivery tube, a drainage tube, a blood circuit, a coating tube, a catheter, a stent, a sheath, a tube connector, an access port, and the like.

The medical device according to embodiments of the present invention may be in the form of a sheet or a film. Specific examples of such embodiment include a skin covering material, a wound dressing material, a protective material for skin, a drug carrier for skin, a biosensor chip, an endoscopic dressing material, and the like.

The medical device according to embodiments of the present invention, the device of the present invention may have a storage container shape. Specific examples of such embodiment include a drug carrier, a cuff, a drainage bag, and the like.

The medical device according to embodiments of the present invention may have a lens shape. Specific examples of such embodiment include ophthalmic lenses such as contact lens, intraocular lens, artificial cornea, corneal inlay, corneal onlay, and eyeglass lens. Among ophthalmic lenses, especially contact lens is one of the most preferred embodiments of the present invention.

Especially, the medical device according to embodiments of the present invention is preferably an ophthalmic lens, a dermal covering material, a wound dressing material, a skin protection material, a skin medicine carrier, an infusion tube, a gas delivery tube, a drain tube, a blood circuit, a covering tube, a catheter, a stent, a sheath biosensor chip, or an endoscopic dressing material.

When the medical device according to embodiments of the present invention is, for example, an ophthalmic device such as a medical device or an ophthalmic lens which is used by being attached to a surface of a living body, the liquid film retention time on the surface of the medical device is preferably long from the viewpoint of preventing from sticking to the skin of users and preventing from sticking to the cornea of wearers. Here, the liquid film retention time is the time period during which a liquid film on the device surface is retained without breaking when the medical device immersed in a phosphate buffer solution is pulled up from the liquid and kept so that the surface is vertical in the air. The liquid film retention time is preferably 15 seconds or more, more preferably 20 seconds or more, and most preferably 30 seconds or more.

When the medical device according to embodiments of the present invention is an ophthalmic device such as an ophthalmic lens, the dynamic contact angle of the medical device surface is preferably low from the viewpoint of preventing from sticking to the cornea of wearers. The dynamic contact angle is preferably 60° or less, more preferably 55° or less, and most preferably 50° or less. The dynamic contact angle (during advancing, immersion rate: 0.1 mm/sec) is measured using a sample wetted with a phosphate buffer solution. Details of the measuring method will be mentioned later.

When the medical device according to embodiments of the present invention is a medical device which is used by being inserted into a living body, or a device used in contact with the mucous membrane, a surface of the medical device preferably has excellent lubricity. An indicator representing the lubricity, the friction coefficient measured by the method mentioned in Examples of the present specification is preferably small. The friction coefficient is preferably 0.7 or less, more preferably 0.6 or less, and most preferably 0.5 or less. If the friction is extremely small, it may be difficult to handle during installing and removing, so that the friction coefficient is preferably 0.001 or more, and more preferably 0.002 or more.

When the medical device is used in an ophthalmic device such as an ophthalmic lens, if the moisture content excessively changed in the production process, there is the fear of poor visibility or deformation of the medical device caused by distortion of a refractive index due to a change in moisture content. From the viewpoint of preventing such problem, the moisture content change rate between the substrate and the resulting medical device is preferably 10 percentage points or less, more preferably 8 percentage points or less, and most preferably 6 percentage points or less. Here, the moisture content change rate (percentage points) means a difference between the moisture content (% by mass) of the resulting medical device and the moisture content (% by mass) of the substrate as a raw material of the medical device. Details of the measuring method will be mentioned later.

The size change rate before and after formation of the hydrophilic polymer layer of the medical device according to embodiments of the present invention is preferably 5% or less, more preferably 4 or less, and most preferably 3% or less, from the viewpoint of preventing corneal injury caused by deformation when used in an ophthalmic device such as an ophthalmic lens. Here, the size change rate before and after formation of a hydrophilic polymer layer means the value in which a change in size of the resulting medical device to the size of the substrate before and after formation of a hydrophilic polymer layer is represented by a rate. Details of the measuring method will be mentioned later.

The tensile elastic modulus of the medical device according to embodiments of the present invention should be appropriately selected according to the type of the medical device. In the case of a soft medical device such as an ophthalmic lens, the tensile elastic modulus is preferably 10 MPa or less, preferably 5 MPa or less, more preferably 3 MPa or less, still more preferably 2 MPa or less, yet more preferably 1 MPa or less, and most preferably 0.6 MPa. The tensile elastic modulus is preferably 0.01 MPa or more, more preferably 0.1 MPa or more, still more preferably 0.2 MPa or more, and most preferably 0.25 MPa or more. In the case of a soft medical device such as an ophthalmic lens, too small tensile elastic modulus may lead to difficulty in handling because of being excessive in softness. Too large tensile elastic modulus may lead to deterioration of comfort because of being excessive in hardness.

The tensile elastic modulus change rate before and after formation of the hydrophilic polymer layer of the medical device according to embodiments of the present invention is preferably 15% or less, more preferably 14% or less, and most preferably 13% or less. Too large tensile elastic modulus change rate may lead to deformation and poor tactile sensation, unfavorably. Here, the tensile elastic modulus change rate before and after formation of the hydrophilic polymer layer means the value in which a change in tensile elastic modulus of the resulting medical device to the tensile elastic modulus of the substrate before and after formation of a hydrophilic polymer layer is represented by a rate. Details of the measuring method will be mentioned later.

The antifouling properties of the medical device of the present invention can be evaluated by the deposition of mucin and deposition of lipid (methyl palmitate). The smaller the deposition amount by these evaluations, the more tactile sensation is excellent and bacterial propagation risk is reduced, favorably. The mucin deposition amount is preferably 10 $\mu g/cm^2$ or less, more preferably 5 $\mu g/cm^2$ or less, and most preferably 3 $\mu g/cm^2$ or less. Details of the measuring method will be mentioned later.

Next, a method of manufacturing a medical device according to embodiments of the present invention will be described. The medical device according to embodiments of the present invention can be obtained by a method in which a substrate is heated in a state of being arranged in a solution containing a hydrophilic polymer having a hydroxyl group and an amide group.

Here, the inventors of the present invention have found that, using an extremely simple method which includes a step of disposing a solution containing a hydrophilic polymer having a hydroxyl group and an amide group and a substrate on or in a support, and heating the solution and the substrate through the support, wherein a pH of the solution before starting the heating step is in a range of 2.0 or higher and 6.0 or lower, and a pH of the solution after completion of the heating step is in a range of 2.0 or higher and 6.0 or lower, the hydrophilic polymer having a hydroxyl group and an amide group can be fixed to a surface of the substrate, thus imparting excellent water wettability, lubricity, and the like to the medical device. Thereby, it is possible to impart excellent water wettability, lubricity, and the like to the medical device without using a conventionally known special method, for example, a method in which the electrostatic adsorption effect using an acidic polymer in combination with a basic polymer is utilized, leading to industrially very important meaning from the viewpoint of shortening the production process.

The support is preferably a mold used for molding a substrate. By using the mold used for molding a substrate as the support, the substrate can be stably arranged in the support. Thereby, it becomes possible to bring a solution containing a hydrophilic polymer having a hydroxyl group and an amide group into uniform contact with the substrate.

Examples of the support include a mold used for molding a substrate of the medical device, a device used in the production process other than molding of a substrate of the medical device, a container used for packing the medical device, and the like.

Although a mold before being used for molding a substrate may be used as the mold, a mold after being used for molding a substrate is preferably used. Reuse of the mold after being used for molding enables production cost reduction and waste reduction.

In an embodiment of the present invention, the support may be disposable. In the present invention, disposable means being disposed after a single use to no more than five uses. In the case of disposal after a single use, there is the convenience of enabling simplification or omission of operations and equipment for returning to the state before use after use of the support. In the case of disposal after two or more and five or less, resources used for the support can be reduced and the amount of the support to be disposed can be reduced, thus providing advantages such as reduction of resource wasting and environmental loading reduction.

When the medical device is a contact lens, the mold used for molding a substrate is preferably a mold used for molding a substrate of the contact lens. The container used for packing the medical device is also preferably a container for the sale of contact lenses. A lens case with contact lens care products used widely for storage is also included.

Hereinafter, mention is made of a specific form of the present invention when the medical device according to embodiments of the present invention is an ophthalmic device such as an ophthalmic lens.

Examples of the mold used for molding a substrate of the medical device include a mold used in methods such as a spin casting method as disclosed in JP 2011-70207 A and a cast mold method as disclosed in JP 2013-222141 A, which are common methods for molding an ophthalmic lens.

It is possible to use, as a material of the above-mentioned mold of the substrate that is used for molding an ophthalmic lens commonly called a mold, any appropriate thermoplastic polyolefin resin or a mixture of such a resin.

Examples of the thermoplastic polyolefin resin include, but are not limited to, a thermoplastic polyethylene resin, a thermoplastic polypropylene resin, a thermoplastic polystyrene resin, and the like, and mixtures thereof.

Examples of an apparatus used in the production process other than molding of a substrate of the medical device include all the apparatuses used in the production process other than molding of a substrate of the medical device, such as an apparatus for transporting an ophthalmic lens, an apparatus for removing an ophthalmic lens from a mold of a substrate, an apparatus used in an extraction step for eliminating an unnecessary residual material in an ophthalmic lens, and an apparatus used in a known surface treatment other than a hydrophilization method of the present invention.

The container used for packing a medical device includes various containers including a vial, a blister container or equivalents thereof. Especially, a so-called blister container is widely used for storage and subdivision of an ophthalmic lens such as a contact lens, as disclosed in JP 2010-508563 W. Usually, a blister container for storage and subdivision of a contact lens comprises a cavity and a base section including a planar flange rising up around the edge of the cavity. The base section is made of a plastic material. A soft cover sheet is adhered to the flange surface to usually seal the cavity in a liquid-tight state. In the cavity of the base section, the contact lens is immersed and accommodated in a lens preservative solution such as various buffer solutions.

The base section may be formed from various plastic materials, and is preferably transparent. The plastic material to be preferably used is sterilizable at 121° C. without substantial loss of its physical properties such as dimensional stability, warpage, and shrinkage. In order to prevent evaporation and loss of the lens preservative solution, a plastic material having low water and vapor permeability is preferably used. In order to prevent contamination and retain the effect of the solution, a plastic material that permeates neither bacteria nor oxygen is preferably used.

Examples of the plastic material include, but are not limited to, fluororesin, polyamide, polyacrylate, polyethylene, nylons, olefin copolymers (e.g., copolymer of polypropylene and polyethylene), polyethylene terephthalate, polyvinyl chloride, amorphous polyolefin, polycarbonate, polysulfone, polybutylene terephthalate, polypropylene, polymethylpentene, polyesters, rubbers, urethanes, and the like. These materials are used alone, or used as a composite or laminated structure. The plastic material constituting the base section is preferably polypropylene.

The cavity of the base section is appropriately designed to store a contact lens and a sufficient amount of lens preservation solution that can completely immerse the contact lens. The cavity may have various shapes including a circular shape, a polygonal shape, an elliptical shape, a heart shape, and the like in a plan view. The surface of the cavity is preferably determined by individual shape, dimension, and the like of an ophthalmic lens stored therein. For example, the surface of the cavity may have a hemispherical (concave) shape.

The cover sheet may be a single film or a multilayer film. Any film may be employed as the cover sheet as long as it can be fixed to the base section by adhesion, welding, or other methods. The cover sheet may be formed of various materials that are impermeable to water and may have various thicknesses. The sheet is preferably sufficiently soft so that the user can easily peel the sheet from the base section. A preferred example of the cover sheet is a laminate layer comprising a layer of a metal foil and at least one, preferably two layers of a polymer such as polypropylene coated with a metal foil. A preferred foil is an aluminum foil.

The base section and the cover sheet may be fixed by various methods. For example, the cover sheet can be secured to the base or its flange by a temperature treatment or ultrasonic treatment, or other appropriate bonding methods.

In the present invention, heating a solution containing a hydrophilic polymer having a hydroxyl group and a substrate through a support means that the solution and the substrate are arranged on or in the support and then heated together with the support.

Next, the molecular weight and the concentration of the hydrophilic polymer will be mentioned. Since the layer does not have sufficient thickness in the prior art, when a polymer layer is formed on a surface of a substrate by using only one hydrophilic polymer having a hydroxyl group, there was a problem that sufficient water wettability and lubricity are not easily imparted to the device. However, regardless of only one hydrophilic polymer having a hydroxyl group in an embodiment of the present invention, it becomes possible to increase the thickness of the layer, thus making it easy to achieve sufficient water wettability and lubricity.

The hydrophilic polymer having a hydroxyl group used in an embodiment of the present invention preferably has a molecular weight of 2,000 to 1,500,000. The molecular weight is more preferably 5,000 or more, and still more preferably 10,000 or more. The molecular weight is more preferably 1,200,000 or less, and still more preferably 1,000,000 or less. Here, a weight average molecular weight in terms of polyethylene glycol measured by a gel permeation chromatography method (aqueous solvent) is used as the molecular weight.

An increase in concentration of the hydrophilic polymer in the solution during the production leads to an increase in thickness of the thus obtained hydrophilic polymer layer. However, too high concentration of the hydrophilic polymer may lead to an increase in difficulty of handling during the production due to an increase in viscosity, so that the concentration in the solution of the hydrophilic polymer having a hydroxyl group is preferably 0.0001 to 30% by mass. The concentration of the hydrophilic polymer is more preferably 0.001% by mass or more, and still more preferably 0.005% by mass or more. The concentration of the hydrophilic polymer is more preferably 20% by mass or less, and still more preferably 15% by mass or less.

In the above heating step, the pH (hereinafter, initial pH) of the solution containing a hydrophilic polymer before start of heating is preferably 2.0 to 6.0 since turbidity does not occur in the solution to obtain a medical device having satisfactory transparency. The initial pH is more preferably 2.2 or higher, still more preferably 2.4 or higher, yet more preferably 2.5 or higher, and further preferably 2.6 or higher. The initial pH is preferably 5.0 or lower, more preferably 4.5 or lower, and still more preferably 4.0 or lower. If the initial pH is 2.0 or higher, turbidity of the solution hardly occurs. It is preferred that turbidity does not occur in the solution because the surface of the medical device may have high water wettability and lubricity. When the initial pH is higher than 6.0, the thus obtained hydrophilic polymer layer may not be separated into two or more layers or two or more phases, leading to deterioration of water wettability and lubricity of the surface of the medical device, unfavorably.

The pH of the solution can be measured using a pH meter (e.g., pH meter Eutech pH 2700 (Eutech Instruments)). Here, the initial pH of a solution containing a hydrophilic polymer having a hydroxyl group means the pH value of the solution measured after adding all the hydrophilic polymer to the solution, followed by stirring at room temperature (23 to 25° C.) for 2 hours with a rotor to thereby make the solution uniform, before disposing a substrate and heating the substrate. In the present invention, the pH value is rounded off to one decimal place.

The pH of the solution can change when a heating operation is performed. The pH of the solution after the heating operation is more preferably 2.0 to 6.0. The pH after heating is more preferably 2.1 or higher, still more preferably 2.2 or higher, and most preferably 2.3 or higher. The pH after heating is more preferably 5.9 or lower, still more preferably 5.5 or lower, yet more preferably 5.0 or lower, and most preferably 4.5 or lower. When the pH of the solution after the heating operation is in the above range, appropriate pH conditions can be obtained while performing the heating operation, thus obtaining suitable physical properties of the thus obtained medical device. After modifying the surface of the substrate used in the medical device by performing the heating operation, the pH can be adjusted by performing a neutralization treatment or adding water. The pH of the solution after performing the heating operation as used herein is the pH before performing such pH adjustment.

A solvent of the solution containing a hydrophilic polymer having a hydroxyl group is preferably water. The pH of the solution is adjusted by adding an acidic substance such as acetic acid, citric acid, formic acid, ascorbic acid, trifluoromethanesulfonic acid, methanesulfonic acid, nitric acid, sulfuric acid, phosphoric acid, or hydrochloric acid to a solution containing a hydrophilic polymer. Of these, an acidic substance selected from citric acid, ascorbic acid, and sulfuric acid are preferable from the viewpoint of low volatility and high safety to a living body. To make it easy to finely adjust the pH, a buffering agent is preferably added to the solution.

It is possible to use, as the buffering agent, any physiologically compatible known buffering agent. An appropriate buffering agent is known to a person with an ordinary skill in the art, and examples thereof include boric acid, borate (e.g., sodium borate), citric acid, citrates (e.g., potassium citrate), bicarbonate (e.g., sodium bicarbonate), phosphate buffer solution (e.g., $Na_2HPO_4$, $NaH_2PO_4$, and $KH_2PO_4$), TRIS (tris(hydroxymethyl)aminomethane), 2-bis(2-hydroxyethyl)amino-2-(hydroxymethyl)-1,3-propanediol, bis-aminopolyol, triethanolamine, ACES (N-(2-acetamide)-2-aminoethanesulfonic acid), BES (N,N-bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS (3-[N-morpholino]-propanesulfonic acid), PIPES (piperazine-N,N'-bis(2-ethanesulfonic acid)), TES (N-[tris(hydroxymethyl)methyl]-2-aminoethanesulfonic acid), and salts thereof. Each buffering agent is used in the effective amount required to achieve desired pH and usually preferably exists in the solution in the amount of 0.001% by mass to 2% by mass. The amount of the buffering agent is more preferably 0.01% by mass or more, and still more preferably 0.05% by mass or more. The amount of the buffering agent is more preferably 1% by mass or less, and still more preferably 0.30% by mass or less.

Examples of the heating method include a high-pressure steam sterilization method, irradiation with electromagnetic waves (γ ray, microwave, etc.), a dry heat method, a flame method, and the like. From the viewpoint of the water wettability, lubricity, and shortening of the production process, a high-pressure steam sterilization method is most preferable. An autoclave is preferably used as an apparatus.

The heating temperature is preferably 60° C. to 200° C. from the viewpoint of obtaining a medical device surface exhibiting satisfactory water wettability and lubricity and exerting less influence on the strength of the medical device itself. The heating temperature is more preferably 80° C. or higher, still more preferably 100° C. or higher, yet more preferably 101° C. or higher, and most preferably 110° C. or higher. The heating temperature is more preferably 180° C. or lower, still more preferably 170° C. or lower, and most preferably 150° C. or lower.

If the heating time is too short, a medical device surface exhibiting satisfactory water wettability and lubricity cannot be obtained. Meanwhile, if the heating time is too long, an adverse influence is exerted on the strength of the medical device itself, the heating time is preferably 5 minutes to 600 minutes. The heating time is more preferably 10 minutes or more, and still more preferably 15 minutes or more. The heating time is more preferably 400 minutes or less, and still more preferably 300 minutes or less.

After the above heat treatment, the medical device thus obtained may be further subjected to the other treatment. Examples of the other treatment include treatments of methods such as a method in which a similar heat treatment is performed in a solution containing a hydrophilic polymer having a hydroxyl group, a method in which a similar heat treatment is performed by using a solution containing no hydrophilic polymer in place of the solution, a method in which irradiation with radiation is performed, a method of performing a layer by layer treatment (LbL treatment) in which each material having an opposite charge is alternately coated one by one, a method in which a crosslinking treatment with metal ions is performed, a method in which a chemical crosslinking treatment is performed, and the like. However, in light of the idea of the present invention which enables hydrophilization of a substrate surface by a simple method, a treatment is preferably performed as long as the production process does not become too complicated.

Radiations used for the above irradiation with radiation are preferably various ion beams, electron beams, positron beams, X-rays, y rays, and neutron rays, more preferably electron rays and y rays, and most preferably y rays.

As the above LbL treatment, for example, a treatment using an acidic polymer and a basic polymer as mentioned in WO 2013/024800 A is preferably used.

Metal ions used for the above crosslinking treatment with metal ions are preferably various metal ions, more preferably monovalent and divalent metal ions, and most preferably divalent metal ions. Alternatively, a chelate complex may also be used.

As the above chemical crosslinking treatment, for example, a reaction between an epoxide group and a carboxyl group as mentioned in JP 2014-533381 W and a crosslinking treatment formed between known appropriate acidic hydrophilic polymers having a hydroxyl group may be used.

In the above method in which a similar heat treatment is performed by using a solution containing no hydrophilic polymer in place of the solution, the solution containing no hydrophilic polymer is not particularly limited and a buffering agent solution is preferable. The above-mentioned substances can be used as the buffering agent.

Here, the pH of the buffering agent solution is preferably within a physiologically acceptable range of 6.3 to 7.8. The pH of the buffering agent solution is preferably 6.5 or higher, and still more preferably 6.8 or higher. The pH of the buffering agent solution is preferably 7.6 or lower, and more preferably 7.4 or lower.

EXAMPLES

The present invention will be described more specifically by way of Examples, but the present invention is not limited to these Examples. First, analytical method and evaluation method will be mentioned.

<Water Wettability (Liquid Film Retention Time)>

A medical device in a storage container was left to stand as it is at room temperature for 24 hours or more. With respect to evaluation of only a commercially available contact lens mentioned in Comparative Examples, the contact lens was lightly washed in 50 mL of a phosphate buffer solution in a beaker at room temperature and then left to stand in 50 mL of a fresh phosphate buffer solution for 24 hours or more.

The medical device was pulled up as it is from the phosphate buffer solution in which the medical device was left to stand and immersed and the time during which the liquid film on the surface was retained in the case of keeping in the air was visually observed, and an average of N=3 was judged according to the following criteria.

A: A liquid film on a surface is retained for 20 seconds or more.

B: A liquid film on a surface breaks after 15 seconds or more and less than 20 seconds.

C: A liquid film on a surface breaks after 5 seconds or more and less than 15 seconds.

D: A liquid film on a surface breaks after 1 second or more and less than 5 seconds.

E: A liquid film on a surface instantly breaks (less than 1 second).

<Lubricity>

A medical device in a storage container was left to stand as it is at room temperature for 24 hours or more. With respect to evaluation of only a commercially available contact lens mentioned in Comparative Examples, the contact lens was lightly washed in 50 mL of a phosphate buffer solution in a beaker at room temperature and then left to stand in 50 mL of a fresh phosphate buffer solution for 24 hours or more.

The medical device was pulled up as it is from the phosphate buffer solution in which the medical device was left to stand and immersed and subjected to sensory evaluation when rubbing with a human finger five times, and then judgment was performed by the following criteria (N=1).

A: There is extremely excellent lubricity (finger slides to flow on a medical device surface and feel no resistance).

B: There is lubricity intermediate between A and C.

C: There is moderate lubricity (finger slides on a medical device surface and hardly feels resistance).

D: Almost no lubricity (intermediate between C and E).

E: No lubricity (finger does not easily slide on a medical device surface and feel large resistance).

<Moisture Content of Substrate and Medical Device>

A substrate was immersed in a phosphate buffer solution and left to stand at room temperature for 24 hours or more. The substrate was pulled out from the phosphate buffer solution and, after wiping off the surface moisture with a wiping cloth ("Kimwipes" (registered trademark) manufactured by NIPPON PAPER CRECIA CO., LTD.), the mass ($W_w$) of the substrate was measured. Thereafter, the substrate was dried at 40° C. for 2 hours in a vacuum dryer and the mass ($W_d$) was measured. From these masses, the moisture content of the substrate was calculated by the following formula (1). The case where the obtained value was less than 1% was judged as below the measurement limit, and the column in the table was filled with "less than 1%". An average of N=3 was regarded as the moisture content. The moisture content of the substrate, i.e., the medical device after the formation of the hydrophilic polymer layer was also calculated in the same manner.

Moisture content (% by mass) of substrate=100× $(W_w-W_d)/W_w$   Formula (1).

<Moisture Content Change Rate Between Substrate and Medical Device>

From the measurement results of the moisture content of the substrate and the medical device, the moisture content change rate was calculated by the following formula (2).

Moisture content change rate (percentage points) between substrate and medical device=moisture content (% by mass) of medical device−moisture content (% by mass) of substrate   Formula (2)

<Contact Angle>

Using, as a sample, a strip-shaped test piece measuring about 5 mm×10 mm×0.1 mm cut out from a sample having a contact lens shape, a dynamic contact angle during advancing to a phosphate buffer solution was measured by a wettability test machine WET-6200 (manufactured by RHESCA CO., LTD.). An immersion rate was 0.1 mm/sec, and an immersion depth was 7 mm.

<Friction Coefficient>

The friction coefficient of the medical device surface wetted with a phosphate buffer solution (preservation solution in a package in the case of measuring only a commercially available contact lens) was measured with N=5 and an average was regarded as the friction coefficient.

Apparatus: Friction tester KES-SE (manufactured by Kato Tech Co., Ltd.)
Friction SENS: H
Measurement SPEED: 2×1 mm/sec
Friction load: 44 g <Lipid Deposition Amount>

In a 20 cc screw tube, 0.03 g of methyl palmitate, 10 g of pure water, and 1 sample having a contact lens shape were placed. The screw tube was shaken for 3 hours under the conditions at 37° C. and 165 rpm. After shaking, the sample in the screw tube was scrubbed with tap water at 40° C. and a household liquid detergent ("Mama Lemon (registered trademark)" manufactured by Lion Corporation). The washed sample was placed in a screw tube containing a phosphate buffer solution and stored in a refrigerator at 4° C. for 1 hour. Thereafter, the sample was visually observed, and if the turbid portion exists, it was judged that methyl palmitate is deposited and the area of the portion in which methyl palmitate is deposited to the entire surface of the sample was observed.

<Mucin Deposition Amount>

A test piece having a width (minimum portion) of 5 mm and a length of 14 mm was cut out from a sample having a contact lens shape using a punching die. Mucin Bovine Submaxillary Gland (Catalog No. 499643) available from CALBIOCHEM was used as mucin. The test piece was immersed in an aqueous mucin solution having a concentration of 0.1% under the conditions for 20 hours at 37° C., and then the amount of mucin deposited to the sample was determined by the bicinchoninic acid (BCA) protein assay method. An average of N=3 was regarded as the mucin deposition amount.

<Tensile Elastic Modulus>

A test piece having a width (minimum part) of 5 mm and a length of 14 mm was cut out from a sample having a contact lens shape using a punching die. Using the test piece, a tensile test was performed using Tensilon Model RTG-1210 manufactured by A&D Company, Limited. A pulling rate was 100 mm/min and a distance between grips (initial) was 5 mm. Measurements were made on both a substrate as a raw material and the resulting medical device. Measurement was made with N=8 and an average of N=6 excluding the maximum value and the minimum value was regarded as the tensile elastic modulus.

<Tensile Elastic Modulus Change Rate Before and After Formation of Hydrophilic Polymer Layer>

From the measurement results of the tensile elastic modulus, calculation was performed by the following formula (3). An average of N=6 was regarded as the tensile elastic modulus change rate before and after the formation of the hydrophilic polymer layer.

Tensile elastic modulus change rate (%) before and after formation of hydrophilic polymer layer= (tensile elastic modulus of medical device−tensile elastic modulus of substrate)/tensile elastic modulus of substrate×100   Formula (3).

<Size>

The diameter of a sample having a contact lens shape was measured and an average of N=3 was regarded as the size. Measurements were made on both a substrate as a raw material and the resulting medical device.

<Size Change Rate Before and After Formation of Hydrophilic Polymer Layer>

From the measurement results of the size, calculation was performed by the following formula (4). An average of N=3 was regarded as the size change rate before and after the formation of a hydrophilic polymer layer.

Size change rate (%) before and after formation of hydrophilic polymer layer=(size of medical device−size of substrate)/size of substrate×100   Formula (4).

<Molecular Weight Measurement>

The molecular weight of a hydrophilic polymer used was measured under the following conditions.
GPC measurement conditions are as follows.
Apparatus: Prominence GPC system manufactured by Shimadzu
Corporation
Pump: LC-20AD
Autosampler: SIL-20AHT
Column oven: CTO-20A
Detector: RID-10A
Column: GMPWXL manufactured by Tosoh Corporation (7.8 mm in inner diameter×30 cm, particle diameter of 13 μm)
Solvent: water/methanol=1/1 (0.1 N lithium nitrate is added)
Flow rate: 0.5 mL/minute
Measurement time: 30 minutes
Sample concentration: 0.1 to 0.3% by mass
Injection amount: 100 μL
Standard sample: Polyethylene oxide standard sample manufactured by Agilent Technologies, Inc. (0.1 kD to 1258 kD)

<pH Measurement Method>

The pH of the solution was measured using a pH meter Eutech pH 2700 (manufactured by Eutech Instruments). In the table, the initial pH of a solution containing a hydrophilic polymer was determined by adding all the hydrophilic polymer to the solution mentioned in each Example, followed by stirring at room temperature (23 to 25° C.) for 2 hours with a rotor to thereby make the solution uniform. In the table, "pH after heat treatment" is the pH measured immediately after the solution was cooled to room temperature (23 to 25° C.) after a heat treatment was performed once.

<Judgment of Separation of Hydrophilic Polymer Layer>

Judgment was made whether or not a hydrophilic polymer layer was separated into two or more layers by observing a cross section of a medical device using a transmission electron microscope.

Apparatus: Transmission electron microscope
Condition: Accelerating voltage of 100 kV
Observation magnification: 8,000 to 100,000 times
Sample preparation: Sample was prepared by a method of staining ultrathin section with $RuO_4$. When it is difficult to discriminate between a substrate and a coat layer, the sample may be stained with $OsO_4$. In this Example, when the substrate is a silicone hydrogel-based or silicone-based substrate, the sample was stained with $RuO_4$. An ultramicrotome was used to fabricate ultrathin section.

<Elemental Composition Analysis of Hydrophilic Polymer Layer>

Elemental composition analysis of a hydrophilic polymer layer was performed by analyzing a cross section of a device frozen in a hydrous state using a cryo-transfer holder by a scanning transmission electron microscope and electron energy loss spectroscopy.
Apparatus: Field emission electron microscope
Conditions: Acceleration voltage: 200 kV
Measurement temperature: about −100° C.
Electron energy-loss spectroscopy: GATAN GIF Tridiem
Image acquisition: Digital Micrograph
Sample preparation: Sample was prepared by a method of staining ultrathin section with $RuO_4$. When it is difficult to discriminate between a substrate and a coat layer, the sample may be stained with $OsO_4$. In this Example, when the substrate is a silicone hydrogel-based or silicone-based substrate, the sample was stained with $RuO_4$. An ultramicrotome was used to fabricate ultrathin section.

<Film Thickness of Hydrophilic Polymer Layer>

The film thickness of a hydrophilic polymer layer in a dry state was measured by observing a cross section of a medical device in a dry state using a transmission electron microscope. Measurement was made under the conditions mentioned in aforementioned <Judgment of Separation of Hydrophilic Polymer Layer>. While changing four places, the film thickness was measured at five places for each field of view, and the film thickness was measured at 20 places in total. The minimum value and the maximum value of the measured film thickness are described.

The film thickness of a hydrophilic polymer layer in a frozen state was obtained by observing a cross section of the Medical device frozen in a water-containing state using a cryotransfer holder using a scanning transmission electron microscope. Measurement was made under the conditions mentioned in aforementioned <Elemental Composition Analysis of Hydrophilic Polymer Layer>. While changing four places, the film thickness was measured at five places for each field of view, and the film thickness was measured at 20 places in total. The minimum value and the maximum value of the measured film thickness are described.

Reference Example 1

After preparing 28 parts by mass of a polydimethylsiloxane having a methacryloyl group at both ends represented by the formula (M1) (FM 7726, JNC Corporation, Mw: 30,000), 7 parts by mass of a silicone monomer represented by the formula (M2) (FM 0721, JNC Corporation, Mw: 5,000), 57.9 parts by mass of trifluoroethyl acrylate ("Viscoat" (registered trademark) 3F, Osaka Organic Chemical Industry Ltd.), 7 parts by mass of 2-ethylhexyl acrylate (Tokyo Chemical Industry Co., Ltd.), and 0.1 part by mass of dimethylaminoethyl acrylate (Kohjin Co., Ltd.), preparing 5,000 ppm of a photoinitiator "IRGACURE" (registered trademark), 819 (NAGASE & CO., LTD.), 5,000 ppm of a UV absorber (RUVA-93, Otsuka Chemical Co., Ltd.), and 100 ppm of a colorant (RB 246, Arran chemical) based on the total amount of these monomers, and preparing 10 parts by mass of t-amyl alcohol based on 100 parts by mass of the total amount of these monomers, all components were mixed, followed by stirring. The mixture thus obtained by stirring was filtered through a membrane filter (pore diameter: 0.45 μm) to remove insoluble substances to obtain a monomer mixture.

The above monomer mixture was poured into a contact lens mold made of a transparent resin (material on base curve side: polypropylene, material on front curve side: polypropylene) and then polymerized by irradiation with light (wavelength 405 nm (±5 nm), illuminance: 0 to 0.7 mW/cm², for 30 minutes).

After the polymerization, the molded article thus obtained was immersed in an aqueous 100% by mass isopropyl alcohol solution at 60° C. for 1.5 hours together with the mold from which a front curve and a base curve were released, and then a molded article having a contact lens shape was removed from the mold. The molded article thus obtained was immersed in a large excess amount of an aqueous 100% by mass isopropyl alcohol solution maintained at 60° C. for 2 hours to extract impurities such as residual monomers. Thereafter, the molded article was dried at room temperature (23° C.) for 12 hours.

[Chemical Formula 1]

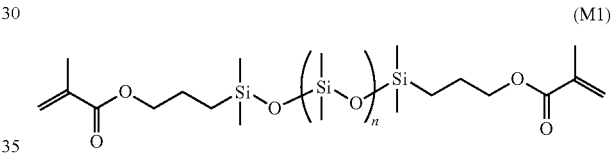

(M1)

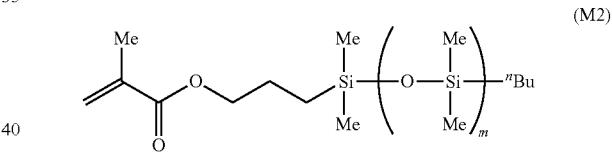

(M2)

[Phosphate Buffer Solution]

Each composition of the phosphate buffer solutions used in the processes of the following Examples and Comparative Examples and the above-mentioned measurements is as follows.
KCl: 0.2 g/L
$KH_2PO_4$: 0.2 g/L
NaCl: 8.0 g/L
$Na_2HPO_4$ (anhydrous): 1.15 g/L
EDTA: 0.25 g/L Example 1

The molded article obtained in Reference Example 1 was used as a substrate. After injecting 1.2 mL of a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in pure water, which has the pH of 2.6 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while immersing for 30 seconds. After replacing the solution in the blister container by a fresh phosphate buffer solution, the molded article was further heated in the autoclave at 121° C. for 30 minutes. The results obtained by evaluation of the molded article using the above method are shown in Tables 1 to 4.

Example 2

The molded article obtained in Reference Example 1 was used as a substrate. After injecting 1.2 mL of a solution containing 0.2% by mass of an acrylic acid/N,N-dimethylacrylamide copolymer (molar ratio in copolymerization: 1/9, Mw: 700,000, manufactured by Osaka Organic Chemical Industry Ltd.) in a phosphate buffer solution, which has the pH of 2.7 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 1 to 4.

Example 3

The molded article obtained in Reference Example 1 was used as a substrate. After injecting 1.2 mL of a solution containing 0.03% by mass of an acrylic acid/N,N-dimethylacrylamide copolymer (molar ratio in copolymerization: 1/2, Mw: 500,000, manufactured by Osaka Organic Chemical Industry Ltd.) in a phosphate buffer solution, which has the pH of 3.1 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 1 to 4.

Example 4

The molded article obtained in Reference Example 1 was used as a substrate. After injecting 1.0 mL of a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution, which has the pH of 2.4 adjusted with sulfuric acid, into the non-molded surface of a polypropylene mold for molding a base curve side of a contact lens, a substrate was placed therein, followed by heating together with the mold in an autoclave at 80° C. for 30 minutes. The molded article thus obtained was washed with a phosphate buffer solution while shaking at 250 rpm for 10 seconds. After replacing the solution in the mold by a fresh phosphate buffer solution, the molded article was further heated in the autoclave at 121° C. for 30 minutes. The results obtained by evaluation of the molded article using the above method are shown in Tables 1 to 4.

Example 5

The molded article obtained in Reference Example 1 was used as a substrate. After injecting 1.2 mL of a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution, which has the pH of 2.4 adjusted with sulfuric acid, into a polypropylene blister container for contact lenses, a substrate was placed in the blister container and the container was sealed, followed by heating together with the container in an autoclave at 100° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 1 to 4.

Example 6

The molded article obtained in Reference Example 1 was used as a substrate. After injecting 1.2 mL of a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in pure water, which has the pH of 2.4 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 1 to 4.

Example 7

A commercially available hydrogel lens containing 2-hydroxyethyl methacrylate as a main component "1-Day Acuvue (registered trademark)" (manufactured by Johnson & Johnson) was used as a substrate. After injecting 1.2 mL of a solution containing 0.1% by mass of an acrylic acid/vinylpyrrolidone copolymer (molar ratio in copolymerization: 1/4, Mw: 500,000, manufactured by Osaka Organic Chemical Industry Ltd.) in a phosphate buffer solution, which has the pH of 3.1 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 1 to 4.

Example 8

A commercially available hydrogel lens containing 2-hydroxyethyl methacrylate as a main component "1-Day Acuvue (registered trademark)" (manufactured by Johnson & Johnson) was used as a substrate. After injecting 1.2 mL of a solution containing 0.1% by mass of an acrylic acid/vinylpyrrolidone copolymer (molar ratio in copolymerization: 1/4, Mw: 500,000, manufactured by Osaka Organic Chemical Industry Ltd.) in a phosphate buffer solution, which has the pH of 4.1 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 1 to 4.

Example 9

A commercially available hydrogel lens containing 2-hydroxyethyl methacrylate as a main component "1-Day Acuvue (registered trademark)" (manufactured by Johnson & Johnson) was used as a substrate. After injecting 1.2 mL of a solution containing 0.1% by mass of an acrylic acid/vinylpyrrolidone copolymer (molar ratio in copolymerization: 1/4, Mw: 500,000, manufactured by Osaka Organic Chemical Industry Ltd.) in a phosphate buffer solution, which has the pH of 5.0 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 1 to 4.

Example 10

A commercially available hydrogel lens containing 2-hydroxyethyl methacrylate as a main component "1-Day Acuvue (registered trademark)" (manufactured by Johnson & Johnson) was used as a substrate. After injecting 1.2 mL of a solution containing 0.1% by mass of an acrylic acid/vinylpyrrolidone copolymer (molar ratio in copolymerization: 1/4, Mw: 500,000, manufactured by Osaka Organic Chemical Industry Ltd.) in a phosphate buffer solution, which has the pH of 5.7 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 1 to 4.

Example 11

A commercially available hydrogel lens containing 2-hydroxyethyl methacrylate as a main component "1-Day Acuvue (registered trademark)" (manufactured by Johnson & Johnson) was used as a substrate. After injecting 1.2 mL of a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution, which has the pH of 3.3 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 1 to 4.

Example 12

A commercially available hydrogel lens containing 2-hydroxyethyl methacrylate as a main component "1-Day Acuvue (registered trademark)" (manufactured by Johnson & Johnson) was used as a substrate. After injecting 1.2 mL of a solution containing 0.2% by mass of an acrylic acid/N,N-dimethylacrylamide copolymer (molar ratio in copolymerization: 1/9, Mw: 500,000, manufactured by Osaka Organic Chemical Industry Ltd.) in a phosphate buffer solution, which has the pH of 3.0 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 1 to 4.

Example 13

A commercially available hydrogel lens containing 2-hydroxyethyl methacrylate as a main component "1-Day Acuvue (registered trademark)" (manufactured by Johnson & Johnson) was used as a substrate. After injecting 1.2 mL of a solution containing 0.2% by mass of an acrylic acid/N,N-dimethylacrylamide copolymer (molar ratio in copolymerization: 1/2, Mw: 700,000, manufactured by Osaka Organic Chemical Industry Ltd.) in a phosphate buffer solution, which has the pH of 3.0 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds.

After replacing the solution in the blister container by a fresh phosphate buffer solution, the molded article was further heated in the autoclave at 121° C. for 30 minutes. The results obtained by evaluation of the molded article using the above method are shown in Tables 1 to 4.

Example 14

A commercially available hydrogel lens containing 2-hydroxyethyl methacrylate as a main component "1-Day Acuvue (registered trademark)" (manufactured by Johnson & Johnson) was used as a substrate. After injecting 1.2 mL of a solution containing 0.1% by mass of an acrylic acid/vinylpyrrolidone copolymer (molar ratio in copolymerization: 1/4, Mw: 500,000, manufactured by Osaka Organic Chemical Industry Ltd.) in a phosphate buffer solution, which has the pH of 4.0 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 1 to 4.

Example 15

A commercially available hydrogel lens containing 2-hydroxyethyl methacrylate as a main component "1-Day Acuvue (registered trademark)" (manufactured by Johnson & Johnson) was used as a substrate. After injecting 1.2 mL of a solution containing 0.1% by mass of an acrylic acid/vinylpyrrolidone copolymer (molar ratio in copolymerization: 1/4, Mw: 800,000, manufactured by Osaka Organic Chemical Industry Ltd.) in a phosphate buffer solution, which has the pH of 4.0 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 1 to 4.

Example 16

A commercially available hydrogel lens containing 2-hydroxyethyl methacrylate as a main component "1-Day Acuvue (registered trademark)" (manufactured by Johnson & Johnson) was used as a substrate. After injecting 1.2 mL of a solution containing 0.1% by mass of an acrylic acid/vinylpyrrolidone copolymer (molar ratio in copolymerization: 1/9, Mw: 400,000, manufactured by Osaka Organic Chemical Industry Ltd.) in a phosphate buffer solution, which has the pH of 4.0 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 1 to 4.

Example 17

A commercially available hydrogel lens containing polyvinylpyrrolidone and silicone as main components "1-Day Acuvue Trueye (registered trademark)" (manufactured by Johnson & Johnson) was used as a substrate. After injecting 1.2 mL of a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution, which has the pH of 3.0 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 1 to 4.

Example 18

A commercially available hydrogel lens containing polyvinylpyrrolidone and silicone as main components "1-Day Acuvue Trueye (registered trademark)" (manufactured by Johnson & Johnson) was used as a substrate. After injecting 1.2 mL of a solution containing 0.2% by mass of an acrylic acid/N,N-dimethylacrylamide copolymer (molar ratio in copolymerization: 1/9, Mw: 500,000, manufactured by Osaka Organic Chemical Industry Ltd.) in a phosphate buffer solution, which has the pH of 3.0 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 1 to 4.

Example 19

A commercially available silicone hydrogel lens containing silicone as a main component "MyDay (registered trademark)" (manufactured by CooperVision, Inc.) was used as a substrate. After injecting 1.0 mL of a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution, which has the pH of 2.0 adjusted with citric acid, into the molded surface of a polypropylene mold for molding a front curve side of a contact lens, a substrate was placed therein, followed by heating together with the mold in an autoclave at 90° C. for 30 minutes. The molded article thus obtained was washed with a phosphate buffer solution while shaking at 250 rpm for 10 seconds. After replacing the solution in the mold by a fresh phosphate buffer solution, the molded article was further heated in the autoclave at 121° C. for 30 minutes. The results obtained by evaluation of the molded article using the above method are shown in Tables 1 to 4.

Example 20

A commercially available silicone hydrogel lens containing silicone as a main component "MyDay (registered trademark)" (manufactured by CooperVision, Inc.) was used as a substrate. After injecting 1.0 mL of a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution, which has the pH of 2.2 adjusted with citric acid, into the molded surface of a polypropylene mold for molding a front curve side of a contact lens, a substrate was placed therein, followed by heating together with the mold in an autoclave at 90° C. for 30 minutes. The molded article thus obtained was washed with a phosphate buffer solution while shaking at 250 rpm for 10 seconds. After replacing the solution in the mold by a fresh phosphate buffer solution, the molded article was further heated in the autoclave at 121° C. for 30 minutes. The results obtained by evaluation of the molded article using the above method are shown in Tables 1 to 4.

Example 21

A commercially available silicone hydrogel lens containing silicone as a main component "MyDay (registered trademark)" (manufactured by CooperVision, Inc.) was used as a substrate. After injecting 1.0 mL of a solution containing 0.4% by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution, which has the pH of 2.0 adjusted with citric acid, into the non-molded surface of a polypropylene mold for molding a base curve side of a contact lens, a substrate was placed therein, followed by heating together with the mold in an autoclave at 90° C. for 30 minutes. The molded article thus obtained was washed with a phosphate buffer solution while shaking at 250 rpm for 10 seconds. After replacing the solution in the mold by a fresh phosphate buffer solution, the molded article was further heated in the autoclave at 121° C. for 30 minutes. The results obtained by evaluation of the molded article using the above method are shown in Tables 1 to 4.

TABLE 1

|  | Substrate | Moisture content of substrate (% by mass) | Hydrophilic polymer and concentration of solution thereof | Initial pH | pH after heating treatment |
|---|---|---|---|---|---|
| Example 1 | Reference Example 1 | Less than 1% | 0.2% by mass Acrylic acid/N,N-dimethylacrylamide copolymer | 2.6 | 5.0 |
| Example 2 | Reference Example 1 | Less than 1% |  | 2.7 | 4.1 |
| Example 3 | Reference Example 1 | Less than 1% | 0.03% by mass Acrylic acid/N,N-dimethylacrylamide copolymer | 3.1 | 3.8 |
| Example 4 | Reference Example 1 | Less than 1% |  | 2.4 | 2.5 |
| Example 5 | Reference Example 1 | Less than 1% | 0.2% by mass Acrylic acid/N,N-dimethylacrylamide copolymer | 2.4 | 2.7 |
| Example 6 | Reference Example 1 | Less than 1% |  | 2.4 | 3.9 |
| Example 7 | "1-Day Acuvue ®" | 58 | 0.1% by mass Acrylic acid/vinylpyrrolidone copolymer | 3.1 | 3.7 |
| Example 8 | "1-Day Acuvue ®" | 58 |  | 4.1 | 4.9 |
| Example 9 | "1-Day Acuvue ®" | 58 |  | 5.0 | 5.4 |
| Example 10 | "1-Day Acuvue ®" | 58 |  | 5.7 | 5.9 |
| Example 11 | "1-Day Acuvue ®" | 58 | 0.2% by mass Acrylic acid/N,N-dimethylacrylamide copolymer | 3.3 | 5.1 |
| Example 12 | "1-Day Acuvue ®" | 58 |  | 3.0 | 4.7 |
| Example 13 | "1-Day Acuvue ®" | 58 | 0.2% by mass Acrylic acid/N,N-dimethylacrylamide copolymer | 3.0 | 4.8 |
| Example 14 | "1-Day Acuvue ®" | 58 | 0.1% by mass Acrylic acid/vinylpyrrolidone copolymer | 4.0 | 4.7 |
| Example 15 | "1-Day Acuvue ®" | 58 |  | 4.0 | 4.8 |
| Example 16 | "1-Day Acuvue ®" | 58 | 0.1% by mass Acrylic acid/vinylpyrrolidone copolymer | 4.0 | 4.9 |
| Example 17 | "1-Day Acuvue ® Trueye" | 46 | 0.2% by mass Acrylic acid/N,N-dimethylacrylamide copolymer | 3.0 | 4.7 |
| Example 18 | "1-Day Acuvue ® Trueye" | 46 |  | 3.0 | 4.6 |
| Example 19 | "MyDay ®" | 54 |  | 2.0 | 2.1 |
| Example 20 | "MyDay ®" | 54 | 0.2% by mass Acrylic acid/N,N-dimethylacrylamide copolymer | 2.2 | 2.3 |
| Example 21 | "MyDay ®" | 54 |  | 2.0 | 2.0 |

TABLE 2

|  | Liquid film retention time (seconds) | Lubricity | Moisture content of device (% by mass) | Number of hydrophilic polymer layers | Results of elemental composition analysis of hydrophilic polymer layer | Moisture content change rate between substrate and device | Contact angle (°) | Friction coefficient |
|---|---|---|---|---|---|---|---|---|
| Example 1 | A (45 seconds) | A | 3.2 | Two layers | Coating polymer was separated into two layers (one layer of which was mixed with substrate) | 3.2 | 49.3 | 0.003 |
| Example 2 | A (40 seconds) | A | 3.2 | Two layers | Coating polymer was separated into two layers (one layer of which was mixed with substrate) | 3.2 | 51.9 | 0.006 |

TABLE 2-continued

| | Liquid film retention time (seconds) | Lubricity | Moisture content of device (% by mass) | Number of hydrophilic polymer layers | Results of elemental composition analysis of hydrophilic polymer layer | Moisture content change rate between substrate and device | Contact angle (°) | Friction coefficient |
|---|---|---|---|---|---|---|---|---|
| Example 3 | A (30 seconds) | A | 4.2 | Two layers | Coating polymer was separated into two layers (one layer of which was mixed with substrate) | 4.2 | 53.8 | 0.004 |
| Example 4 | B (19 seconds) | A | 4.0 | Two layers | Coating polymer was separated into two layers (one layer of which was mixed with substrate) | 4.0 | 54.8 | 0.012 |
| Example 5 | B (19 seconds) | A | 5.4 | Two layers | Coating polymer was separated into two layers (one layer of which was mixed with substrate) | 5.4 | 49.1 | 0.018 |
| Example 6 | A (40 seconds) | A | 9.1 | Two layers | Coating polymer was separated into two layers (one layer of which was mixed with substrate) | 9.1 | 42.0 | 0.005 |
| Example 7 | A (120 seconds or more) | A | 59 | Two layers | Coating polymer mixed with substrate and coating polymer alone | 1.0 | 40.7 | 0.009 |
| Example 8 | A (120 seconds or more) | A | 58 | Two layers | Coating polymer mixed with substrate and coating polymer alone | 1.0 | 50.5 | 0.444 |
| Example 9 | A (120 seconds or more) | A | 58 | Two layers | Coating polymer mixed with substrate and coating polymer alone | 0.8 | 51.8 | 0.611 |
| Example 10 | A (120 seconds or more) | C | 58 | Two layers | Coating polymer mixed with substrate and coating polymer alone | 0.8 | 52.4 | 0.615 |
| Example 11 | A (120 seconds or more) | A | 58 | Two layers | Coating polymer mixed with substrate and coating polymer alone | 1.1 | 39.0 | 0.300 |
| Example 12 | A (120 seconds or more) | A | 58 | Two layers | Coating polymer mixed with substrate and coating polymer alone | 0.9 | 39.0 | 0.180 |
| Example 13 | A (120 seconds or more) | A | 58 | Two layers | Coating polymer mixed with substrate and coating polymer alone | 0.8 | 38.3 | 0.050 |
| Example 14 | A (120 seconds or more) | B | 58 | Two layers | Coating polymer mixed with substrate and coating polymer alone | 1.5 | 44.6 | 0.295 |
| Example 15 | A (120 seconds or more) | B | 58 | Two layers | Coating polymer mixed with substrate and coating polymer alone | 1.1 | 54.6 | 0.090 |
| Example 16 | A (120 seconds or more) | A | 58 | Two layers | Coating polymer mixed with substrate and coating polymer alone | 1.0 | 51.4 | 0.160 |
| Example 17 | A (100 seconds) | A | 46.6 | Two layers | Coating polymer mixed with substrate and coating polymer alone | 0.6 | 46.3 | 0.220 |
| Example 18 | A (120 seconds or more) | A | 46.4 | Two layers | Coating polymer mixed with substrate and coating polymer alone | 0.4 | 45.8 | 0.390 |
| Example 19 | A (87 seconds) | A | 54.5 | Two layers | Coating polymer mixed with substrate and coating polymer alone | 0.5 | 48.0 | 0.03 |
| Example 20 | A (49 seconds) | A | 54.6 | Two layers | Coating polymer mixed with substrate and coating polymer alone | 0.6 | 47.5 | 0.018 |
| Example 21 | A (78 seconds) | A | 54.7 | Two layers | Coating polymer mixed with substrate and coating polymer alone | 0.7 | 47.8 | 0.024 |

TABLE 3

| | Lipid deposition amount | Mucin deposition amount (μg/cm$^2$) | Tensile elastic modulus of substrate (MPa) | Tensile elastic modulus of device (MPa) | Tensile elastic modulus change rate before and after formation of hydrophilic polymer layer (%) |
|---|---|---|---|---|---|
| Example 1 | Not deposited | 8.56 | 0.53 | 0.49 | −6.7 |
| Example 2 | Not deposited | 6.18 | 0.53 | 0.49 | −6.7 |
| Example 3 | Not deposited | 9.50 | 0.53 | 0.49 | −6.7 |
| Example 4 | Not deposited | 1.57 | 0.53 | 0.49 | −6.7 |
| Example 5 | Not deposited | 1.53 | 0.53 | 0.49 | −6.7 |
| Example 6 | Not deposited | 5.70 | 0.53 | 0.49 | −6.7 |
| Example 7 | Not deposited | 3.25 | 0.30 | 0.26 | −13.1 |
| Example 8 | Not deposited | 1.94 | 0.30 | 0.26 | −13.1 |

TABLE 3-continued

|  | Lipid deposition amount | Mucin deposition amount (µg/cm$^2$) | Tensile elastic modulus of substrate (MPa) | Tensile elastic modulus of device (MPa) | Tensile elastic modulus change rate before and after formation of hydrophilic polymer layer (%) |
|---|---|---|---|---|---|
| Example 9 | Not deposited | 2.68 | 0.30 | 0.26 | −13.1 |
| Example 10 | Not deposited | 2.86 | 0.30 | 0.26 | −13.1 |
| Example 11 | Not deposited | 2.78 | 0.30 | 0.28 | −6.8 |
| Example 12 | Not deposited | 3.65 | 0.30 | 0.28 | −6.8 |
| Example 13 | Not deposited | 9.00 | 0.30 | 0.28 | −6.8 |
| Example 14 | Not deposited | 1.53 | 0.30 | 0.26 | −13.1 |
| Example 15 | Not deposited | 3.48 | 0.30 | 0.26 | −13.1 |
| Example 16 | Not deposited | 3.26 | 0.30 | 0.26 | −13.1 |
| Example 17 | Not deposited | 2.85 | 0.70 | 0.71 | 0.40 |
| Example 18 | Not deposited | 3.05 | 0.70 | 0.71 | 0.40 |
| Example 19 | Not deposited | 3.15 | 0.61 | 0.61 | 0.7 |
| Example 20 | Not deposited | 2.24 | 0.61 | 0.60 | −0.9 |
| Example 21 | Not deposited | 3.01 | 0.61 | 0.61 | 0.2 |

TABLE 4

|  | Size of substrate (mm) | Size of device (mm) | Size change rate before and after formation of hydrophilic polymer layer (%) | Film thickness dry state of hydrophilic polymer layer (nm) | Film thickness frozen state of hydrophilic polymer layer (nm) |
|---|---|---|---|---|---|
| Example 1 | 14.00 | 14.01 | 0.1 | 10 to 17 | 30 to 45 |
| Example 2 | 14.00 | 14.01 | 0.1 | 11 to 16 | 32 to 48 |
| Example 3 | 14.00 | 14.01 | 0.1 | 5 to 12 | 30 to 43 |
| Example 4 | 14.00 | 14.01 | 0.1 | 15 to 20 | 34 to 46 |
| Example 5 | 14.00 | 14.01 | 0.1 | 10 to 20 | 29 to 41 |
| Example 6 | 14.00 | 14.01 | 0.1 | 15 to 25 | 28 to 39 |
| Example 7 | 14.20 | 13.90 | −2.1 | 15 to 20 | 40 to 53 |
| Example 8 | 14.20 | 13.90 | −2.1 | 10 to 18 | 41 to 51 |
| Example 9 | 14.20 | 13.90 | −2.1 | 8 to 15 | 30 to 40 |
| Example 10 | 14.20 | 13.90 | −2.1 | 5 to 10 | 29 to 44 |
| Example 11 | 14.20 | 13.95 | −1.8 | 22 to 35 | 42 to 56 |
| Example 12 | 14.20 | 13.95 | −1.8 | 20 to 35 | 45 to 59 |
| Example 13 | 14.20 | 13.95 | −1.8 | 22 to 40 | 40 to 50 |
| Example 14 | 14.20 | 13.90 | −2.1 | 22 to 37 | 40 to 55 |
| Example 15 | 14.20 | 13.90 | −2.1 | 20 to 40 | 35 to 45 |
| Example 16 | 14.20 | 13.90 | −2.1 | 20 to 35 | 40 to 51 |
| Example 17 | 14.20 | 14.23 | 0.2 | 10 to 17 | 70 to 98 |
| Example 18 | 14.20 | 14.23 | 0.2 | 10 to 20 | 80 to 95 |
| Example 19 | 14.20 | 14.12 | −0.6 | 10 to 15 | 40 to 50 |
| Example 20 | 14.20 | 14.14 | −0.4 | 11 to 14 | 42 to 50 |
| Example 21 | 14.20 | 14.13 | −0.5 | 8 to 16 | 30 to 42 |

Comparative Example 1

The molded article obtained in Reference Example 1 was used as a substrate. After injecting 1.2 mL of a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution (pH 6.8) into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking for at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 5 to 8.

Comparative Example 2

The molded article obtained in Reference Example 1 was used as a substrate. After injecting 1.2 mL of a solution, prepared by adjusting the pH of a phosphate buffer solution to 2.7 with citric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 5 to 8.

Comparative Example 3

The molded article obtained in Reference Example 1 was used as a substrate. After injecting 1.0 mL of a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution (pH 6.8) into the non-molded surface of a polypropylene mold for molding a base curve side of a contact lens, a substrate was placed therein and then left to stand and immersed at room temperature (23° C.) overnight. The molded article thus obtained was washed with a phosphate buffer solution while shaking at 250 rpm for 10 seconds. After replacing the solution in the blister container by a fresh phosphate buffer solution, the molded article was heated in an autoclave at 121° C. for 30 minutes. The results obtained by evaluation of the molded article using the above method are shown in Tables 5 to 8.

Comparative Example 4

A commercially available hydrogel lens containing 2-hydroxyethyl methacrylate as a main component "1-Day Acuvue (registered trademark)" (manufactured by Johnson & Johnson) was used as a substrate. After injecting 1.0 mL of a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution (pH 6.8) into the non-molded surface of a polypropylene mold for molding a base curve side of a contact lens, a substrate was placed therein and then left to stand and immersed at room temperature (23° C.) overnight. The molded article thus obtained was washed with a phosphate buffer solution while shaking at 250 rpm for 10 seconds. After replacing the solution in the mold by a fresh phosphate buffer solution, the molded article was heated in an autoclave at 121° C. for 30 minutes. The results obtained by evaluation of the molded article using the above method are shown in Tables 5 to 8.

Comparative Example 5

The molded article obtained in Reference Example 1 was used as a substrate. After injecting 1.2 mL of a solution containing 0.1% by mass of polyacrylic acid "Sokalan (registered trademark) PA110S" (Mw: 250,000, manufactured by BASF) in a phosphate buffer solution (pH 5.3) into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 5 to 8.

Comparative Example 6

The molded article obtained in Reference Example 1 was used as a substrate. After injecting 1.2 mL of a solution containing 0.2% by mass of polydimethylacrylamide (Mw: 360,000, manufactured by Osaka Organic Chemical Industry Ltd.) in a phosphate buffer solution, which has the pH of 2.5 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 5 to 8.

Comparative Example 7

The molded article obtained in Reference Example 1 was used as a substrate. After injecting 1.2 mL of a solution containing 0.2% by mass of polyvinylpyrrolidone K-90 (Mw: 360,000, manufactured by Tokyo Chemical Industry Co., Ltd.) in a phosphate buffer solution, which has the pH of 2.5 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 5 to 8.

Comparative Example 8

The molded article obtained in Reference Example 1 was used as a substrate. After injecting 1.2 mL of a solution containing 0.2% by mass of Polyethylene Glycol 200 (Mw: 180 to 200, manufactured by Wako Pure Chemical Industries, Ltd.) in a phosphate buffer solution, which has the pH of 2.5 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 5 to 8.

Comparative Example 9

The molded article obtained in Reference Example 1 was used as a substrate. After injecting 1.0 mL of a solution containing 0.2% by mass of poly-N-vinylacetamide "GE-191-103" (Mw: 1,000,000, manufactured by Showa Denko K.K.) in a phosphate buffer solution, which has the pH of 2.5 adjusted with sulfuric acid, into the molded surface of a mold for molding a front curve side of a contact lens (made of polypropylene), a substrate was placed therein and the mold was covered with the molded surface of a mold for molding a base curve side, followed by heating together with the mold in an autoclave at 121° C. for 30 minutes. The molded article thus obtained was washed with a phosphate buffer solution while shaking at 250 rpm for 10 seconds. After replacing the solution in the mold by a fresh phosphate buffer solution, the molded article was further heated in the autoclave at 121° C. for 30 minutes. The results obtained by evaluation of the molded article using the above method are shown in Tables 5 to 8.

Comparative Example 10

The molded article obtained in Reference Example 1 was used as a substrate. After making a trial of immersing the substrate in a solution containing 0.1% by mass of polyvinyl alcohol (Mw: 31,000 to 50,000, manufactured by SIGMA-ALDRICH) in a phosphate buffer solution, a precipitate was formed in the solution due to inferior solubility of polyvinyl alcohol, thus failing to perform coating.

Comparative Example 11

The molded article obtained in Reference Example 1 was used as a substrate. After injecting 1.0 mL of a solution containing 0.2% by mass of "Methyl Cellulose 400" (Mw: 84,000, manufactured by Wako Pure Chemical Industries, Ltd.) in a phosphate buffer solution, which has the pH of 2.5 adjusted with sulfuric acid, into the molded surface of a mold for molding a front curve side of a contact lens (made of polypropylene), a substrate was placed therein and the mold was covered with the molded surface of a mold for molding a base curve side, followed by heating together with the mold in an autoclave at 121° C. for 30 minutes. The molded article thus obtained was washed with a phosphate buffer solution while shaking at 250 rpm for 10 seconds. After replacing the solution in the mold by a fresh phosphate buffer solution, the molded article was further heated in the autoclave at 121° C. for 30 minutes. The results obtained by evaluation of the molded article using the above method are shown in Tables 5 to 8.

Comparative Example 12

The molded article obtained in Reference Example 1 was used as a substrate. After injecting 1.0 mL of a solution containing 0.2% by mass of Poloxamer 407 (Mw: 11,500, manufactured by BASF) in a phosphate buffer solution, which has the pH of 2.5 adjusted with sulfuric acid, into the molded surface of a mold for molding a front curve side of a contact lens (made of polypropylene), a substrate was placed therein and the mold was covered with the molded surface of a mold for molding a base curve side, followed by heating together with the mold in an autoclave at 121° C. for 30 minutes. The molded article thus obtained was washed with a phosphate buffer solution while shaking at 250 rpm for 10 seconds. After replacing the solution in the mold by a fresh phosphate buffer solution, the molded article was further heated in the autoclave at 121° C. for 30 minutes. The results obtained by evaluation of the molded article using the above method are shown in Tables 5 to 8.

Comparative Example 13

The molded article obtained in Reference Example 1 was used as a substrate. After injecting 1.0 mL of a solution containing 0.2% by mass of sodium alginate (manufactured by SHOWA CHEMICAL CO., LTD.) in a phosphate buffer solution, which has the pH of 2.5 adjusted with sulfuric acid, into the molded surface of a mold for molding a front curve side of a contact lens (made of polypropylene), a substrate was placed therein and the mold was covered with the molded surface of a mold for molding a base curve side, followed by heating together with the mold in an autoclave at 121° C. for 30 minutes. The molded article thus obtained was washed with a phosphate buffer solution while shaking at 250 rpm for 10 seconds. After replacing the solution in the mold by a fresh phosphate buffer solution, the molded article was further heated in the autoclave at 121° C. for 30 minutes. The results obtained by evaluation of the molded article using the above method are shown in Tables 5 to 8.

Comparative Example 14

The molded article obtained in Reference Example 1 was used as a substrate. After injecting 1.2 mL of a solution containing 0.05% by mass of poly-2-acrylamido-2-methyl-propanesulfonic acid (Mw: 200,000, manufactured by oneself) in a phosphate buffer solution (pH 6.8) into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 5 to 8.

Comparative Example 15

The molded article obtained in Reference Example 1 was used as a substrate. After injecting 1.2 mL of a solution containing 0.05% by mass of poly-2-acrylamido-2-methyl-propanesulfonic acid/N,N-dimethylacrylamide copolymer (molar ratio in copolymerization: 1/9, Mw: 200,000, manufactured by oneself) in a phosphate buffer solution (pH 6.8) into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 5 to 8.

Comparative Example 16

The molded article obtained in Reference Example 1 was used as a substrate. After injecting 1.2 mL of a solution containing 0.2% by mass of a polyvinyl acetate/polyvinylpyrrolidone copolymer "PVA-6450" (Mw: 50,000, manufactured by Osaka Organic Chemical Industry Ltd.) in a phosphate buffer solution, which has the pH of 2.5 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 5 to 8.

Comparative Example 17

A commercially available hydrogel lens containing 2-hydroxyethyl methacrylate as a main component "1-Day Acuvue (registered trademark)" (manufactured by Johnson & Johnson) was used as a substrate. After injecting 1.2 mL of a solution containing 0.2% by mass of a polyvinyl acetate/polyvinylpyrrolidone copolymer "PVA-6450" (Mw: 50,000, manufactured by Osaka Organic Chemical Industry Ltd.) in a phosphate buffer solution, which has the pH of 2.5 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 5 to 8.

Comparative Example 18

A commercially available silicone hydrogel lens containing polyvinylpyrrolidone and silicone as main components "1-Day Acuvue Trueye (registered trademark)" (manufactured by Johnson & Johnson) was used as a substrate. After injecting 1.0 mL of a solution containing 0.2% by mass of a polyvinyl acetate/polyvinylpyrrolidone copolymer "PVA-6450" (Mw: 50,000, manufactured by Osaka Organic Chemical Industry Ltd.) in a phosphate buffer solution, which has the pH of 2.5 adjusted with sulfuric acid, into the molded surface of a mold for molding a front curve side of a contact lens (made of polypropylene), a substrate was placed therein and the mold was covered with the molded surface of a mold for molding a base curve side, followed by heating together with the mold in an autoclave at 121° C. for 30 minutes. The molded article thus obtained was washed with a phosphate buffer solution while shaking at 250 rpm for 10 seconds. After replacing the solution in the mold by a fresh phosphate buffer solution, the molded article was further heated in the autoclave at 121° C. for 30 minutes. The results obtained by evaluation of the molded article using the above method are shown in Tables 5 to 8.

Comparative Example 19

A commercially available hydrogel lens containing 2-hydroxyethyl methacrylate as a main component "1-Day Acuvue (registered trademark)" (manufactured by Johnson & Johnson) was used as a substrate. After injecting 1.2 mL of a solution containing 0.2% by mass of poly-N-vinylacetamide "GE-191-103" (Mw: 1,000,000, manufactured by Showa Denko K.K.) in a phosphate buffer solution, which has the pH of 2.5 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 5 to 8.

Comparative Example 20

A commercially available silicone hydrogel lens containing polyvinylpyrrolidone and silicone as main components "1-Day Acuvue Trueye (registered trademark)" (manufactured by Johnson & Johnson) was used as a substrate. After injecting 1.2 mL of a solution containing 0.2% by mass of poly-N-vinylacetamide "GE-191-103" (Mw: 1,000,000, manufactured by Showa Denko K.K.) in a phosphate buffer solution, which has the pH of 2.5 adjusted with sulfuric acid, into a polypropylene blister container for contact lenses, a substrate was placed in the blister container and the container was sealed, followed by heating together with the container in an autoclave at 121° C. for 30 minutes. The molded article thus obtained was washed with a phosphate buffer solution while shaking at 250 rpm for 10 seconds. After replacing the solution in the blister container by a fresh phosphate buffer solution, the molded article was further heated in the autoclave at 121° C. for 30 minutes. The results obtained by evaluation of the molded article using the above method are shown in Tables 5 to 8.

Comparative Example 21

A commercially available hydrogel lens containing 2-hydroxyethyl methacrylate as a main component "1-Day Acuvue (registered trademark)" (manufactured by Johnson & Johnson) was used as a substrate. After injecting 1.0 mL of a solution containing 0.2% by mass of sodium alginate (manufactured by SHOWA CHEMICAL CO., LTD.) in a phosphate buffer solution, which has the pH of 2.5 adjusted with sulfuric acid, into the molded surface of a mold for molding a front curve side of a contact lens (made of polypropylene), a substrate was placed therein and the mold was covered with the molded surface of a mold for molding a base curve side, followed by heating together with the mold in an autoclave at 121° C. for 30 minutes. The molded article thus obtained was washed with a phosphate buffer solution while shaking at 250 rpm for 10 seconds. After replacing the solution in the mold by a fresh phosphate buffer solution, the molded article was further heated in the autoclave at 121° C. for 30 minutes. The results obtained by evaluation of the molded article using the above method are shown in Tables 5 to 8.

TABLE 5

| | Substrate | Moisture content of substrate (% by mass) | Hydrophilic polymer and concentration of solution thereof | Initial pH | pH after heating treatment |
|---|---|---|---|---|---|
| Comparative Example 1 | Reference Example 1 | Less than 1% | 0.2% by mass Acrylic acid/N,N-dimethylacrylamide copolymer | 6.8 | 6.9 |
| Comparative Example 2 | Reference Example 1 | Less than 1% | Containing no polymer | 2.7 | 2.8 |

TABLE 5-continued

|  | Substrate | Moisture content of substrate (% by mass) | Hydrophilic polymer and concentration of solution thereof | Initial pH | pH after heating treatment |
|---|---|---|---|---|---|
| Comparative Example 3 | Reference Example 1 | Less than 1% | 0.2% by mass Acrylic acid/N,N-dimethylacrylamide copolymer | 6.8 | 6.83 |
| Comparative Example 4 | "1-Day Acuvue ®" | 58 | 0.2% by mass Acrylic acid/N,N-dimethylacrylamide copolymer | 6.8 | 6.9 |
| Comparative Example 5 | Reference Example 1 | Less than 1% | 0.1% by mass Polyacrylic acid | 5.3 | 5.3 |
| Comparative Example 6 | Reference Example 1 | Less than 1% | 0.2% by mass Polydimethylacrylamide | 2.5 | 2.5 |
| Comparative Example 7 | Reference Example 1 | Less than 1% | 0.2% by mass Polyvinylpyrrolidone | 2.5 | 2.5 |
| Comparative Example 8 | Reference Example 1 | Less than 1% | 0.2% by mass Polyethylene glycol 200 | 2.5 | 2.5 |
| Comparative Example 9 | Reference Example 1 | Less than 1% | 0.2% by mass Poly-N-vinylacetamide | 2.5 | 2.5 |
| Comparative Example 10 | Reference Example 1 | Less than 1% | 0.1% by mass Polyvinyl alcohol | *Impossible to perform coating due to inferior solubility | *Impossible to perform coating due to inferior solubility |
| Comparative Example 11 | Reference Example 1 | Less than 1% | 0.2% by mass Methyl Cellulose 400 | 2.5 | 2.5 |
| Comparative Example 12 | Reference Example 1 | Less than 1% | 0.2% by mass Poloxamer 407 | 2.5 | 2.5 |
| Comparative Example 13 | Reference Example 1 | Less than 1% | 0.2% by mass Sodium alginate | 2.5 | 2.5 |
| Comparative Example 14 | Reference Example 1 | Less than 1% | 0.05% by mass Poly-2-acrylamido-2-methylpropanesulfonic acid | 6.8 | 6.9 |
| Comparative Example 15 | Reference Example 1 | Less than 1% | 0.05% by mass 2-Acrylamido-2-methylpropanesulfonic acid/N,Ndimethylacrylamide copolymer | 6.8 | 6.9 |
| Comparative Example 16 | Reference Example 1 | Less than 1% | 0.2% by mass Vinylpyrrolidone/vinyl acetate copolymer | 2.5 | 2.4 |
| Comparative Example 17 | "1-Day Acuvue ®" | 58 | 0.2% by mass Vinylpyrrolidone/vinyl acetate copolymer | 2.5 | 2.6 |
| Comparative Example 18 | "1-Day Acuvue ® Trueye" | 46 | 0.2% by mass Vinylpyrrolidone/vinyl acetate copolymer | 2.5 | 2.6 |
| Comparative Example 19 | "1-Day Acuvue ®" | 58 | 0.2% by mass Poly-N-vinylacetamide | 2.5 | 2.5 |
| Comparative Example 20 | "1-Day Acuvue ® Trueye" | 46 | 0.2% by mass Poly-N-vinylacetamide | 2.5 | 2.5 |
| Comparative Example 21 | "1-Day Acuvue ®" | 58 | 0.2% by mass Sodium alginate | 2.5 | 2.6 |

TABLE 6

|  | Liquid film retention time (seconds) | Lubricity | Moisture content of device (% by mass) | Number of hydrophilic polymer layers | Moisture content change rate between substrate and medical device | Contact angle (°) | Friction coefficient |
|---|---|---|---|---|---|---|---|
| Comparative Example 1 | E (0 second) | D | Less than 1% | Impossible to confirm layer | 0 | 83.0 | 0.850 |
| Comparative Example 2 | E (0 second) | E | Less than 1% | 0 | None | 81.9 | 0.852 |
| Comparative Example 3 | E (0 second) | E | Less than 1% | Impossible to confirm layer | 0 | 80.0 | 0.852 |
| Comparative Example 4 | A (20 seconds) | E | 58% | Impossible to confirm layer | 0 | 54.0 | 0.677 |
| Comparative Example 5 | E (0 second) | E | Less than 1% | Impossible to confirm layer | 0 | 79.0 | 0.849 |
| Comparative Example 6 | E (0 second) | E | Less than 1% | Impossible to confirm layer | 0 | 82.0 | 0.840 |
| Comparative Example 7 | E (0 second) | E | Less than 1% | Impossible to confirm layer | 0 | 80.9 | 0.839 |
| Comparative Example 8 | E (0 second) | E | Less than 1% | Impossible to confirm layer | 0 | 81.9 | 0.850 |
| Comparative Example 9 | E (0 second) | E | Less than 1% | Impossible to confirm layer | 0 | 83.5 | 0.830 |

TABLE 6-continued

|  | Liquid film retention time (seconds) | Lubricity | Moisture content of device (% by mass) | Number of hydrophilic polymer layers | Moisture content change rate between substrate and medical device | Contact angle (°) | Friction coefficient |
|---|---|---|---|---|---|---|---|
| Comparative Example 10 | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility |
| Comparative Example 11 | E (0 second) | E | Less than 1% | Impossible to confirm layer | 0 | 83.0 | 0.860 |
| Comparative Example 12 | E (0 second) | E | Less than 1% | Impossible to confirm layer | 0 | 82.9 | 0.841 |
| Comparative Example 13 | E (0 second) | E | Less than 1% | Impossible to confirm layer | 0 | 80.1 | 0.852 |
| Comparative Example 14 | E (0 second) | E | Less than 1% | Impossible to confirm layer | 0 | 78.0 | 0.854 |
| Comparative Example 15 | E (0 second) | E | Less than 1% | Impossible to confirm layer | 0 | 81.7 | 0.830 |
| Comparative Example 16 | E (0 second) | E | Less than 1% | Impossible to confirm layer | 0 | 80.0 | 0.820 |
| Comparative Example 17 | A (20 seconds) | D | 58 | Impossible to confirm layer | 0 | 53.5 | 0.450 |
| Comparative Example 18 | C (12 seconds) | C | 46 | Impossible to confirm layer | 0 | 48.0 | 0.130 |
| Comparative Example 19 | C (10 seconds) | D | 58 | Impossible to confirm layer | 0 | 54.0 | 0.470 |
| Comparative Example 20 | C (12 seconds) | C | 46 | Impossible to confirm layer | 0 | 47.0 | 0.120 |
| Comparative Example 21 | C (10 seconds) | D | 58 | Impossible to confirm layer | 0 | 53.9 | 0.419 |

TABLE 7

|  | Lipid deposition amount | Mucin deposition amount ($\mu g/cm^2$) | Tensile elastic modulus of substrate (MPa) | Tensile elastic modulus of device (MPa) | Tensile elastic modulus change rate before and after formation of hydrophilic polymer layer (%) |
|---|---|---|---|---|---|
| Comparative Example 1 | Deposited on entire surface | 3.20 | 0.53 | 0.49 | −6.8 |
| Comparative Example 2 | Deposited on entire surface | 3.00 | 0.53 | None | None |
| Comparative Example 3 | Deposited on entire surface | 2.95 | 0.53 | 0.49 | −6.8 |
| Comparative Example 4 | Not deposited | 2.88 | 0.30 | 0.28 | −6.8 |
| Comparative Example 5 | Deposited on entire surface | 3.35 | 0.53 | 0.49 | −6.8 |
| Comparative Example 6 | Deposited on entire surface | 3.00 | 0.53 | 0.49 | −6.8 |
| Comparative Example 7 | Deposited on entire surface | 3.10 | 0.53 | 0.49 | −6.8 |
| Comparative Example 8 | Deposited on entire surface | 2.98 | 0.53 | 0.49 | −6.8 |
| Comparative Example 9 | Deposited on entire surface | 3.40 | 0.53 | 0.49 | −6.8 |
| Comparative Example 10 | *Impossible to perform coating due to inferior solubility | *Impossible to perform coating due to inferior solubility | 0.53 | *Impossible to perform coating due to inferior solubility | *Impossible to perform coating due to inferior solubility |
| Comparative Example 11 | Deposited on entire surface | 3.29 | 0.53 | 0.49 | −6.8 |
| Comparative Example 12 | Deposited on entire surface | 2.99 | 0.53 | 0.49 | −6.8 |
| Comparative Example 13 | Deposited on entire surface | 3.04 | 0.53 | 0.49 | −6.8 |
| Comparative Example 14 | Deposited on entire surface | 3.00 | 0.53 | 0.49 | −6.8 |
| Comparative Example 15 | Deposited on entire surface | 3.30 | 0.53 | 0.49 | −6.8 |
| Comparative Example 16 | Deposited on entire surface | 2.91 | 0.42 | 0.49 | 15.1 |

TABLE 7-continued

|  | Lipid deposition amount | Mucin deposition amount ($\mu g/cm^2$) | Tensile elastic modulus of substrate (MPa) | Tensile elastic modulus of device (MPa) | Tensile elastic modulus change rate before and after formation of hydrophilic polymer layer (%) |
|---|---|---|---|---|---|
| Comparative Example 17 | Not deposited | 2.25 | 0.30 | 0.28 | −7.7 |
| Comparative Example 18 | Deposited in area accounting for 1/5 of entire area | 1.00 | 0.70 | 0.60 | −15.3 |
| Comparative Example 19 | Not deposited | 2.30 | 0.30 | 0.29 | −4.4 |
| Comparative Example 20 | Deposited in area accounting for 1/5 of entire area | 1.10 | 0.70 | 0.71 | 0.40 |
| Comparative Example 21 | Not deposited | 2.20 | 0.30 | 0.29 | −4.4 |

TABLE 8

|  | Size of substrate (mm) | Size of device (mm) | Size change rate before and after formation of hydrophilic polymer layer (%) | Film thickness dried state of hydrophilic polymer layer (nm) | Film thickness frozen state of hydrophilic polymer layer (nm) |
|---|---|---|---|---|---|
| Comparative Example 1 | 14.00 | 14.01 | 0.1 | 0 | 0 |
| Comparative Example 2 | 14.00 | None | None | 0 | 0 |
| Comparative Example 3 | 14.00 | 14.01 | 0.1 | 0 | 0 |
| Comparative Example 4 | 14.20 | 14.05 | −1.1 | 0 | 0 |
| Comparative Example 5 | 14.00 | 14.00 | 0.0 | 0 | 0 |
| Comparative Example 6 | 14.00 | 14.00 | 0.0 | 0 | 0 |
| Comparative Example 7 | 14.00 | 14.00 | 0.0 | 0 | 0 |
| Comparative Example 8 | 14.00 | 14.00 | 0.0 | 0 | 0 |
| Comparative Example 9 | 14.00 | 14.00 | 0.0 | 0 | 0 |
| Comparative Example 10 | 14.00 | *Impossible to perform coating due to inferior solubility | *Impossible to perform coating due to inferior solubility | *Impossible to perform coating due to inferior solubility | *Impossible to perform coating due to inferior solubility |
| Comparative Example 11 | 14.00 | 14.00 | 0.0 | 0 | 0 |
| Comparative Example 12 | 14.00 | 14.00 | 0.0 | 0 | 0 |
| Comparative Example 13 | 14.00 | 14.00 | 0.0 | 0 | 0 |
| Comparative Example 14 | 14.00 | 14.00 | 0.0 | 0 | 0 |
| Comparative Example 15 | 14.00 | 14.00 | 0.0 | 0 | 0 |
| Comparative Example 16 | 14.00 | 14.00 | 0.0 | 0 | 0 |
| Comparative Example 17 | 14.20 | 13.90 | −2.1 | 0 | 0 |
| Comparative Example 18 | 14.20 | 14.3 | 0.7 | 0 | 0 |
| Comparative Example 19 | 14.20 | 14.10 | −0.7 | 0 | 0 |
| Comparative Example 20 | 14.20 | 14.20 | 0.0 | 0 | 0 |
| Comparative Example 21 | 14.20 | 14.10 | −0.7 | 0 | 0 |

Comparative Example 22

A commercially available silicone hydrogel lens containing polyvinylpyrrolidone and silicone as main components "1-Day Acuvue Trueye (registered trademark)" (manufactured by Johnson & Johnson) was used as a substrate. After injecting 1.0 mL of a solution containing 0.2% by mass of sodium alginate (manufactured by SHOWA CHEMICAL CO., LTD.) in a phosphate buffer solution, which has the pH of 2.5 adjusted with sulfuric acid, into the molded surface of a mold for molding a front curve side of a contact lens (made of polypropylene), a substrate was placed therein and the mold was covered with the molded surface of a mold for molding a base curve side, followed by heating together with the mold in an autoclave at 121° C. for 30 minutes. The molded article thus obtained was washed with a phosphate buffer solution while shaking at 250 rpm for 10 seconds. After replacing the solution in the mold by a fresh phosphate buffer solution, the molded article was further heated in the autoclave at 121° C. for 30 minutes. The results obtained by evaluation of the molded article using the above method are shown in Tables 9 to 12.

Comparative Example 23

A commercially available hydrogel lens containing 2-hydroxyethyl methacrylate as a main component "1-Day Acuvue (registered trademark)" (manufactured by Johnson & Johnson) was used as a substrate. After injecting 1.0 mL of a solution containing 0.2% by mass of Poloxamer 407 (Mw: 11,500, manufactured by BASF) in a phosphate buffer solution, which has the pH of 2.5 adjusted with sulfuric acid, into the molded surface of a mold for molding a front curve side of a contact lens (made of polypropylene), a substrate was placed therein and the mold was covered with the molded surface of a mold for molding a base curve side, followed by heating together with the mold in an autoclave at 121° C. for 30 minutes. The molded article thus obtained was washed with a phosphate buffer solution while shaking at 250 rpm for 10 seconds. After replacing the solution in the mold by a fresh phosphate buffer solution, the molded article was further heated in the autoclave at 121° C. for 30 minutes. The results obtained by evaluation of the molded article using the above method are shown in Tables 9 to 12.

Comparative Example 24

A commercially available silicone hydrogel lens containing polyvinylpyrrolidone and silicone as main components "1-Day Acuvue Trueye (registered trademark)" (manufactured by Johnson & Johnson) was used as a substrate. After injecting 1.0 mL of a solution containing 0.2% by mass of Poloxamer 407 (Mw: 11,500, manufactured by BASF Japan) in a phosphate buffer solution, which has the pH of 2.5 adjusted with sulfuric acid, into the molded surface of a mold for molding a front curve side of a contact lens (made of polypropylene), a substrate was placed therein and the mold was covered with the molded surface of a mold for molding a base curve side, followed by heating together with the mold in an autoclave at 121° C. for 30 minutes. The molded article thus obtained was washed with a phosphate buffer solution while shaking at 250 rpm for 10 seconds. After replacing the solution in the mold by a fresh phosphate buffer solution, the molded article was further heated in the autoclave at 121° C. for 30 minutes. The results obtained by evaluation of the molded article using the above method are shown in Tables 9 to 12.

Comparative Example 25

A commercially available hydrogel lens containing 2-hydroxyethyl methacrylate as a main component "1-Day Acuvue (registered trademark)" (manufactured by Johnson & Johnson) was used as a substrate. After injecting 1.0 mL of a solution containing 0.05% by mass of poly-2-acrylamido-2-methylpropanesulfonic acid (Mw: 200,000, manufactured by oneself) in a phosphate buffer solution (pH 6.8) into the molded surface of a mold for molding a front curve side of a contact lens (made of polypropylene), a substrate was placed therein and the mold was covered with the molded surface of a mold for molding a base curve side, followed by heating together with the mold in an autoclave at 121° C. for 30 minutes. The molded article thus obtained was washed with a phosphate buffer solution while shaking at 250 rpm for 10 seconds. After replacing the solution in the mold by a fresh phosphate buffer solution, the molded article was further heated in the autoclave at 121° C. for 30 minutes. The results obtained by evaluation of the molded article using the above method are shown in Tables 9 to 12.

Comparative Example 26

A commercially available silicone hydrogel lens containing polyvinylpyrrolidone and silicone as main components "1-Day Acuvue Trueye (registered trademark)" (manufactured by Johnson & Johnson) was used as a substrate. After injecting 1.0 mL of a solution containing 0.05% by mass of poly-2-acrylamido-2-methylpropanesulfonic acid (Mw: 200,000, manufactured by oneself) in a phosphate buffer solution (pH 6.8) into the molded surface of a mold for molding a front curve side of a contact lens (made of polypropylene), a substrate was placed therein and the mold was covered with the molded surface of a mold for molding a base curve side, followed by heating together with the mold in an autoclave at 121° C. for 30 minutes. The molded article thus obtained was washed with a phosphate buffer solution while shaking at 250 rpm for 10 seconds. After replacing the solution in the mold by a fresh phosphate buffer solution, the molded article was further heated in the autoclave at 121° C. for 30 minutes. The results obtained by evaluation of the molded article using the above method are shown in Tables 9 to 12.

Comparative Example 27

A commercially available hydrogel lens containing 2-hydroxyethyl methacrylate as a main component "1-Day Acuvue (registered trademark)" (manufactured by Johnson & Johnson) was used as a substrate. After injecting 1.0 mL of a solution containing 0.05% by mass of a poly-2-acrylamido-2-methylpropanesulfonic acid/N,N-dimethylacrylamide copolymer (molar ratio in copolymerization: 1/9, Mw: 200,000, manufactured by oneself) in a phosphate buffer solution (pH 6.8) into the molded surface of a mold for molding a front curve side of a contact lens (made of polypropylene), a substrate was placed therein and the mold was covered with the molded surface of a mold for molding a base curve side, followed by heating together with the mold in an autoclave at 121° C. for 30 minutes. The molded article thus obtained was washed with a phosphate buffer solution while shaking at 250 rpm for 10 seconds. After replacing the solution in the mold by a fresh phosphate buffer solution, the molded article was further heated in the autoclave at 121° C. for 30 minutes. The results obtained by evaluation of the molded article using the above method are shown in Tables 9 to 12.

Comparative Example 28

A commercially available silicone hydrogel lens containing polyvinylpyrrolidone and silicone as main components "1-Day Acuvue Trueye (registered trademark)" (manufactured by Johnson & Johnson) was used as a substrate. After injecting 1.0 mL of a solution containing 0.05% by mass of a poly-2-acrylamido-2-methylpropanesulfonic acid/N,N-dimethylacrylamide copolymer (molar ratio in copolymerization: 1/9, Mw: 200,000, manufactured by oneself) in a phosphate buffer solution (pH 6.8) into the molded surface of a mold for molding a front curve side of a contact lens (made of polypropylene) after using for molding the substrate of Reference Example 1, a substrate was placed therein and the mold was covered with the molded surface of a mold for molding a base curve side, followed by heating together with the mold in an autoclave at 121° C. for 30 minutes. The molded article thus obtained was washed with a phosphate buffer solution while shaking at 250 rpm for 10 seconds. After replacing the solution in the mold by a fresh phosphate buffer solution, the molded article was further heated in the autoclave at 121° C. for 30 minutes. The results obtained by evaluation of the molded article using the above method are shown in Tables 9 to 12.

Comparative Example 29

The molded article obtained in Reference Example 1 was used as a substrate. After injecting 1.0 mL of an aqueous solution containing 0.1% by mass of an acrylic acid/vinylpyrrolidone copolymer (molar ratio in copolymerization: 1/9, Mw: 400,000, manufactured by Osaka Organic Chemical Industry Ltd.) and 0.3% by mass of urea in pure water, which has the pH of 3.8 adjusted with sulfuric acid, into the molded surface of a mold for molding a front curve side of a contact lens (made of polypropylene) after using for molding the substrate of Reference Example 1, a substrate was placed therein and the mold was covered with the molded surface of a mold for molding a base curve side, followed by heating together with the mold in an autoclave at 121° C. for 30 minutes. The molded article thus obtained was washed with a phosphate buffer solution while shaking at 250 rpm for 30 seconds. After replacing the solution in the mold by a fresh phosphate buffer solution, the molded article was further heated in the autoclave at 121° C. for 30 minutes. The results obtained by evaluation of the molded article using the above method are shown in Tables 9 to 12.

Comparative Example 30

A commercially available hydrogel lens containing 2-hydroxyethyl methacrylate as a main component "Medalist (registered trademark) 1DAY PLUS" (manufactured by Bausch & Lomb Incorporated) was used as a substrate. After injecting 1.0 mL of an aqueous solution containing 0.1% by mass of an acrylic acid/vinylpyrrolidone copolymer (molar ratio in copolymerization: 1/9, Mw: 400,000, manufactured by Osaka Organic Chemical Industry Ltd.) and 0.3% by mass of urea in pure water, which has the pH of 3.8 adjusted with sulfuric acid, into the molded surface of a mold for molding a front curve side of a contact lens (made of polypropylene) after using for molding the substrate of Reference Example 1, a substrate was placed therein and the mold was covered with the molded surface of a mold for molding a base curve side, followed by heating together with the mold in an autoclave at 121° C. for 30 minutes. The molded article thus obtained was washed with a phosphate buffer solution while shaking at 250 rpm for 30 seconds. After replacing the solution in the mold by a fresh phosphate buffer solution, the molded article was further heated in the autoclave at 121° C. for 30 minutes. The results obtained by evaluation of the molded article using the above method are shown in Tables 9 to 12.

Comparative Example 31

A commercially available silicone hydrogel lens containing polyvinylpyrrolidone and silicone as main components "1-Day Acuvue Trueye (registered trademark)" (manufactured by Johnson & Johnson) was used as a substrate. After injecting 1.0 mL of an aqueous solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) and 0.3% by mass of urea in pure water, which has the pH of 3.0 adjusted with sulfuric acid, into the molded surface of a mold for molding a front curve side of a contact lens (made of polypropylene) after using for molding the substrate of Reference Example 1, a substrate was placed therein and the mold was covered with the molded surface of a mold for molding a base curve side, followed by heating together with the mold in an autoclave at 121° C. for 30 minutes. The molded article thus obtained was washed with a phosphate buffer solution while shaking at 250 rpm for 30 seconds. After replacing the solution in the mold by a fresh phosphate buffer solution, the molded article was further heated in the autoclave at 121° C. for 30 minutes. The results obtained by evaluation of the molded article using the above method are shown in Tables 9 to 12.

Comparative Example 32

The results obtained by evaluation of a commercially available hydrogel lens containing 2-hydroxyethyl methacrylate as a main component "1-Day Acuvue (registered trademark)" (manufactured by Johnson & Johnson) using the above method are shown in Tables 9 to 12.

Comparative Example 33

The results obtained by evaluation of a commercially available silicone hydrogel lens containing polyvinylpyrrolidone and silicone as main components "1-Day Acuvue Trueye (registered trademark)" (manufactured by Johnson & Johnson) using the above method are shown in Tables 9 to 12.

Comparative Example 34

The results obtained by evaluation of a commercially available silicone hydrogel lens containing polyvinylpyrrolidone and silicone as main components "Acuvue Oasys (registered trademark)" (manufactured by Johnson & Johnson) using the above method are shown in Tables 9 to 12.

Comparative Example 35

The results obtained by evaluation of a commercially available silicone hydrogel lens, which has a surface subjected to a plasma treatment and contains silicone as a main component "AIR OPTIX (registered trademark) EXAQUA" (manufactured by Alcon Japan Ltd.), using the above method are shown in Tables 9 to 12.

Comparative Example 36

The results obtained by evaluation of a commercially available hydrogel lens containing 2-hydroxyethyl methacrylate obtained by copolymerizing an MPC monomer (2-methacryloyloxyethylphosphorylcholine) as a main component "Proclear (registered trademark) 1 Day" (manufactured by Cooper Vision) using the above method are shown in Tables 9 to 12.

Comparative Example 37

The molded article obtained in Reference Example 1 Polyacrylic acid "Sokalan (registered trademark) PA110S" (Mw: 250,000, manufactured by BASF) was used as a substrate. After injecting 1.0 mL of a solution containing 1.2% by mass of Polyacrylic acid "Sokalan (registered trademark) PA110S" (Mw: 250,000, manufactured by BASF) in pure water (pH 2.6) into the non-molded surface of a mold for molding a base curve side of a contact lens (made of polypropylene), a substrate was placed therein and then immersed at 37° C. for 30 minutes. The molded article thus obtained was washed in pure water while shaking at 250 rpm for 10 seconds, followed by replacing the solution in the mold by a fresh phosphate buffer solution. The results obtained by evaluation of the molded article using the above method are shown in Tables 9 to 12.

Comparative Example 38

A commercially available hydrogel lens containing 2-hydroxyethyl methacrylate as a main component "1-Day Acuvue (registered trademark)" (manufactured by Johnson & Johnson) was used as a substrate. After injecting 1.0 mL of a solution containing 1.2% by mass of polyacrylic acid "Sokalan (registered trademark) PA110S" (Mw: 250,000, manufactured by BASF Japan) in pure water (pH 2.6) into the non-molded surface of a mold for molding a base curve side of a contact lens (made of polypropylene), a substrate was placed therein and then immersed at 37° C. for 30 minutes. The molded article thus obtained was washed in pure water while shaking at 250 rpm for 10 seconds, followed by replacing the solution in the mold by a fresh phosphate buffer solution. The results obtained by evaluation of the molded article using the above method are shown in Tables 9 to 12.

Comparative Example 39

A commercially available silicone hydrogel lens containing polyvinylpyrrolidone and silicone as main components "1-Day Acuvue Trueye (registered trademark)" (manufactured by Johnson & Johnson) was used as a substrate. After injecting 1.0 mL of a solution containing 1.2% by mass of polyacrylic acid "Sokalan (registered trademark) PA110S" (Mw: 250,000, manufactured by BASF) in pure water (pH 2.6) into the non-molded surface of a mold for molding a base curve side of a contact lens (made of polypropylene), a substrate was placed therein and then immersed at 37° C. for 30 minutes. The molded article thus obtained was washed in pure water while shaking at 250 rpm for 10 seconds, followed by replacing the solution in the mold by a fresh phosphate buffer solution. The results obtained by evaluation of the molded article using the above method are shown in Tables 9 to 12.

Comparative Example 40

The molded article obtained in Reference Example 1 was used as a substrate. After injecting 1.0 mL of an aqueous solution containing hydrochloric acid (pH 3.0) into the non-molded surface of a mold for molding a base curve side of a contact lens (made of polypropylene), a substrate was arranged on the non-molded surface, immersed at room temperature for 5 minutes and then washed in pure water while shaking at 250 rpm for 10 seconds. After injecting 1.0 mL of a solution containing 0.1% by mass of polyacrylic acid "Sokalan (registered trademark) PA110S" (Mw: 250,000, manufactured by BASF) in pure water (pH 3.3) into the non-molded surface of a mold for molding a base curve side of a contact lens (made of polypropylene), a substrate was placed therein and then immersed at room temperature for 5 minutes. The molded article thus obtained was washed in pure water while shaking at 250 rpm for 10 seconds, followed by replacing the solution in the mold by a fresh phosphate buffer solution. The results obtained by evaluation of the molded article using the above method are shown in Tables 9 to 12.

Comparative Example 41

A commercially available hydrogel lens containing 2-hydroxyethyl methacrylate as a main component "1-Day Acuvue (registered trademark)" (manufactured by Johnson & Johnson) was used as a substrate. After injecting 1.0 mL of an aqueous solution containing hydrochloric acid (pH 3.0) into the non-molded surface of a mold for molding a base curve side of a contact lens (made of polypropylene), a substrate was placed therein, immersed at room temperature for 5 minutes and then washed in pure water while shaking at 250 rpm for 10 seconds. After replacing the solution in the mold by 1.0 mL of a solution containing 0.1% by mass of polyacrylic acid "Sokalan (registered trademark) PA110S" (Mw: 250,000, manufactured by BASF) in pure water (pH 3.3), a substrate was immersed at room temperature for 5 minutes. The molded article thus obtained was washed in pure water while shaking at 250 rpm for 10 seconds, followed by replacing the solution in the mold by a fresh phosphate buffer solution. The results obtained by evaluation of the molded article using the above method are shown in Tables 9 to 12.

Comparative Example 42

A commercially available silicone hydrogel lens containing polyvinylpyrrolidone and silicone as main components "1-Day Acuvue Trueye (registered trademark)" (manufactured by Johnson & Johnson) was used as a substrate. After injecting 1.0 mL of an aqueous solution containing hydrochloric acid (pH 3.0) into the non-molded surface of a mold for molding a base curve side of a contact lens (made of polypropylene), a substrate was placed therein, immersed at room temperature for 5 minutes and then washed in pure water while shaking at 250 rpm for 10 seconds. After replacing the solution in the mold by 1.0 mL of a solution containing 0.1% by mass of polyacrylic acid "Sokalan (registered trademark) PA110S" (Mw: 250,000, manufactured by BASF) in pure water (pH 3.3), a substrate was immersed at room temperature for 5 minutes. The molded article thus obtained was washed in pure water while shaking at 250 rpm for 10 seconds, followed by replacing the solution in the mold by a fresh phosphate buffer solution. The results obtained by evaluation of the molded article using the above method are shown in Tables 9 to 12.

Comparative Example 43

The molded article obtained in Reference Example 1 was used as a substrate. After making a trial of immersing the substrate in a solution containing 0.1% by mass of chitosan (0.5% in 0.5% Acetic Acid at 20° C.) (manufactured by TCI Corporation) in pure water, a precipitate was formed in the solution due to inferior solubility of chitosan, thus failing to perform coating.

Comparative Example 44

The results obtained by evaluation of a commercially available hydrogel lens containing 2-hydroxyethyl methacrylate as a main component "Medalist (registered trademark) 1DAY PLUS" (manufactured by Bausch & Lomb Incorporated), using the above method are shown in Tables 9 to 12.

TABLE 9

| | Substrate | Moisture content of substrate (% by mass) | Hydrophilic polymer and concentration of solution thereof | Initial pH | pH after heating treatment |
|---|---|---|---|---|---|
| Comparative Example 22 | "1-Day Acuvue ® Trueye" | 46 | 0.2% by mass Sodium alginate | 2.5 | 2.6 |
| Comparative Example 23 | "1-Day Acuvue ®" | 58 | 0.2% by mass Poloxamer 407 | 2.5 | 2.5 |
| Comparative Example 24 | "1-Day Acuvue ® Trueye" | 46 | 0.2% by mass Poloxamer 407 | 2.5 | 2.5 |
| Comparative Example 25 | "1-Day Acuvue ®" | 58 | 0.05% by mass Poly-2-acrylamido-2-methylpropanesulfonic acid | 6.8 | 6.9 |
| Comparative Example 26 | "1-Day Acuvue ® Trueye" | 46 | 0.05% by mass Poly-2-acrylamido-2-methylpropanesulfonic acid | 6.8 | 6.9 |
| Comparative Example 27 | "1-Day Acuvue ®" | 58 | 0.05% by mass 2-Acrylamido-2-methylpropanesulfonic acid/N,Ndimethylacrylamide copolymer | 6.8 | 6.9 |
| Comparative Example 28 | "1-Day Acuvue ® Trueye" | 46 | 0.05% by mass 2-Acrylamido-2-methylpropanesulfonic acid/N,Ndimethylacrylamide copolymer | 6.8 | 6.9 |
| Comparative Example 29 | Reference Example 1 | Less than 1% | 0.1% by mass Acrylic acid/vinylpyrrolidone copolymer Urea: 0.3% by mass | 3.8 | 7.0 |
| Comparative Example 30 | "Medalist ® 1DAY PLUS" | 59 | 0.1% by mass Acrylic acid/vinylpyrrolidone copolymer Urea: 0.3% by mass | 3.8 | 7.0 |
| Comparative Example 31 | "1-Day Acuvue ® Trueye" | 46 | 0.2% by mass Acrylic acid/N,N-dimethylacrylamide copolymer, Urea: 0.3% by mass | 3.0 | 7.0 |
| Comparative Example 32 | "1-Day Acuvue ®" | 58 | None | None | None |
| Comparative Example 33 | "1-Day Acuvue ® Trueye" | 46 | None | None | None |
| Comparative Example 34 | "Acuvue Oasys ®" | 38 | None | None | None |
| Comparative Example 35 | "AIR OPTIX ® EXAQUA" | 24 | None | None | None |
| Comparative Example 36 | "Proclear ® 1 Day" | 60 | None | None | None |
| Comparative Example 37 | Reference Example 1 | Less than 1% | 1.2% by mass Polyacrylic acid | None | None |
| Comparative Example 38 | "1-Day Acuvue ®" | 58 | 1.2% by mass Polyacrylic acid | None | None |
| Comparative Example 39 | "1-Day Acuvue ® Trueye" | 46 | 1.2% by mass Polyacrylic acid | None | None |
| Comparative Example 40 | Reference Example 1 | Less than 1% | 0.1% by mass Polyacrylic acid | None | None |
| Comparative Example 41 | "1-Day Acuvue ®" | 58 | 0.1% by mass Polyacrylic acid | None | None |
| Comparative Example 42 | "1-Day Acuvue ® Trueye" | 46 | 0.1% by mass Polyacrylic acid | None | None |
| Comparative Example 43 | Reference Example 1 | Less than 1% | 0.1% by mass chitosan | *Impossible to perform coating due to inferior solubility | *Impossible to perform coating due to inferior solubility |
| Comparative Example 44 | "Medalist ® 1DAY PLUS" | 59 | None | None | None |

TABLE 10

| | Liquid film retention time (seconds) | Lubricity | Moisture content of device (%) | Number of hydrophilic polymer layers | Moisture content change rate between substrate and medical device | Contact angle (°) | Friction coefficient |
|---|---|---|---|---|---|---|---|
| Comparative Example 22 | C (5 seconds) | C | 46 | Impossible to confirm layer | 0 | 46.0 | 0.110 |
| Comparative Example 23 | A (20 seconds) | D | 58 | Impossible to confirm layer | 0 | 52.1 | 0.445 |
| Comparative Example 24 | C (5 seconds) | C | 46 | Impossible to confirm layer | 0 | 46.8 | 0.105 |
| Comparative Example 25 | A (20 seconds) | D | 58 | Impossible to confirm layer | 0 | 52.0 | 0.450 |
| Comparative Example 26 | D (4 seconds) | C | 46 | Impossible to confirm layer | 0 | 46.5 | 0.109 |

TABLE 10-continued

|  | Liquid film retention time (seconds) | Lubricity | Moisture content of device (%) | Number of hydrophilic polymer layers | Moisture content change rate between substrate and medical device | Contact angle (°) | Friction coefficient |
|---|---|---|---|---|---|---|---|
| Comparative Example 27 | A (20 seconds) | D | 58 | Impossible to confirm layer | 0 | 52.1 | 0.450 |
| Comparative Example 28 | D (3 seconds) | C | 46 | Impossible to confirm layer | 0 | 46.1 | 0.105 |
| Comparative Example 29 | D (1 second) | E | Less than 1% | Impossible to confirm layer | 0 | 81.9 | 0.830 |
| Comparative Example 30 | B (15 seconds) | D | 59 | Impossible to confirm layer | 0 | 76.0 | 0.350 |
| Comparative Example 31 | D (2 seconds) | D | 46 | Impossible to confirm layer | 0 | 47.0 | 0.105 |
| Comparative Example 32 | A (20 seconds) | D | 58 | Impossible to confirm layer | None | 52.1 | 0.434 |
| Comparative Example 33 | D (3 seconds) | C | 46 | Impossible to confirm layer | None | 46.5 | 0.190 |
| Comparative Example 34 | A (20 seconds) | C | 38 | Impossible to confirm layer | None | 50.4 | 0.107 |
| Comparative Example 35 | D (4 seconds) | D | 24 | Impossible to confirm layer | None | 53.2 | 0.774 |
| Comparative Example 36 | D (4 seconds) | D | 60 | Impossible to confirm layer | None | 55.5 | 0.321 |
| Comparative Example 37 | E (0 second) | E | Less than 1% | Impossible to confirm layer | 0 | 75.0 | 0.834 |
| Comparative Example 38 | A (83 seconds) | D | 58 | Impossible to confirm layer | 0 | 45.1 | 0.201 |
| Comparative Example 39 | C (14 seconds) | C | 46 | Impossible to confirm layer | 0 | 40.0 | 0.100 |
| Comparative Example 40 | E (0 second) | E | Less than 1% | Impossible to confirm layer | 0 | 78.5 | 0.833 |
| Comparative Example 41 | A 70 seconds) | D | 58 | Impossible to confirm layer | 0 | 42.0 | 0.210 |
| Comparative Example 42 | B (17 seconds) | C | 46 | Impossible to confirm layer | 0 | 40.3 | 0.102 |
| Comparative Example 43 | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility |
| Comparative Example 44 | A (120 seconds) | D | 60 | Impossible to confirm layer | None | 74.6 | 0.380 |

TABLE 11

|  | Lipid deposition amount | Mucin deposition amount (µg/cm$^2$) | Tensile elastic modulus of substrate (MPa) | Tensile elastic modulus of device (MPa) | Tensile elastic modulus change rate before and after formation of hydrophilic polymer layer (%) |
|---|---|---|---|---|---|
| Comparative Example 22 | Deposited in area accounting for 1/5 of entire area | 1.01 | 0.70 | 0.71 | 0.40 |
| Comparative Example 23 | Not deposited | 2.30 | 0.30 | 0.29 | −4.4 |
| Comparative Example 24 | Deposited in area accounting for 1/5 of entire area | 0.99 | 0.70 | 0.71 | 0.40 |
| Comparative Example 25 | Not deposited | 2.20 | 0.30 | 0.29 | −4.4 |
| Comparative Example 26 | Deposited in area accounting for 1/5 of entire area | 0.99 | 0.70 | 0.71 | 0.40 |
| Comparative Example 27 | Not deposited | 2.09 | 0.30 | 0.29 | −4.4 |
| Comparative Example 28 | Deposited in area accounting for 1/5 of entire area | 1.02 | 0.70 | 0.71 | 0.40 |
| Comparative Example 29 | Deposited on entire area | 3.09 | 0.53 | 0.49 | −6.8 |
| Comparative Example 30 | Not deposited | 2.60 | 0.26 | 0.27 | 5.1 |
| Comparative Example 31 | Deposited in area accounting for 1/5 of entire area | 1.04 | 0.70 | 0.71 | 0.40 |
| Comparative Example 32 | Not deposited | 2.10 | 0.30 | None | None |

TABLE 11-continued

|  | Lipid deposition amount | Mucin deposition amount ($\mu g/cm^2$) | Tensile elastic modulus of substrate (MPa) | Tensile elastic modulus of device (MPa) | Tensile elastic modulus change rate before and after formation of hydrophilic polymer layer (%) |
| --- | --- | --- | --- | --- | --- |
| Comparative Example 33 | Deposited in area accounting for ⅓ of entire area | 0.94 | 0.70 | None | None |
| Comparative Example 34 | Not deposited | 1.18 | 0.70 | None | None |
| Comparative Example 35 | Not deposited | 2.59 | 1.47 | None | None |
| Comparative Example 36 | Not deposited | 5.07 | 0.39 | None | None |
| Comparative Example 37 | Deposited on entire area | 4.00 | 0.53 | 0.51 | −2.7 |
| Comparative Example 38 | Not deposited | 3.20 | 0.30 | 0.29 | −2.3 |
| Comparative Example 39 | Deposited in area accounting for ⅓ of entire area | 3.50 | 0.70 | 0.71 | 1.3 |
| Comparative Example 40 | Deposited on entire area | 3.89 | 0.53 | 0.53 | 1.3 |
| Comparative Example 41 | Not deposited | 2.99 | 0.30 | 0.29 | −4.2 |
| Comparative Example 42 | Deposited in area accounting for ⅓ of entire area | 3.90 | 0.70 | 0.73 | 3.3 |
| Comparative Example 43 | *Impossible to perform coating due to inferior solubility | *Impossible to perform coating due to inferior solubility | 0.53 | *Impossible to perform coating due to inferior solubility | *Impossible to perform coating due to inferior solubility |
| Comparative Example 44 | Not deposited | 2.47 | 0.26 | None | None |

TABLE 12

|  | Size of substrate (mm) | Size of device (mm) | Size change rate before and after formation of hydrophilic polymer layer (%) | Film thickness dried state of hydrophilic polymer layer (nm) | Film thickness frozen state of hydrophilic polymer layer (nm) |
| --- | --- | --- | --- | --- | --- |
| Comparative Example 22 | 14.20 | 14.20 | 0.0 | 0 | 0 |
| Comparative Example 23 | 14.20 | 14.10 | −0.7 | 0 | 0 |
| Comparative Example 24 | 14.20 | 14.20 | 0.0 | 0 | 0 |
| Comparative Example 25 | 14.20 | 14.10 | −0.7 | 0 | 0 |
| Comparative Example 26 | 14.20 | 14.20 | 0.0 | 0 | 0 |
| Comparative Example 27 | 14.20 | 14.10 | −0.7 | 0 | 0 |
| Comparative Example 28 | 14.20 | 14.20 | 0.0 | 0 | 0 |
| Comparative Example 29 | 14.00 | 14.00 | 0.0 | 0 | 0 |
| Comparative Example 30 | 14.00 | 14.00 | 0.0 | 0 | 0 |
| Comparative Example 31 | 14.20 | 14.10 | −0.7 | 0 | 0 |
| Comparative Example 32 | 14.20 | None | None | 0 | 0 |
| Comparative Example 33 | 14.20 | None | None | 0 | 0 |
| Comparative Example 34 | 14.00 | None | None | 0 | 0 |
| Comparative Example 35 | 13.80 | None | None | 0 | 0 |
| Comparative Example 36 | 14.20 | None | None | 0 | 0 |
| Comparative Example 37 | 14.00 | 14.00 | 0.0 | 0 | 0 |
| Comparative Example 38 | 14.20 | 14.10 | −0.7 | 0 | 0 |
| Comparative Example 39 | 14.20 | 14.20 | 0.0 | 0 | 0 |

TABLE 12-continued

|  | Size of substrate (mm) | Size of device (mm) | Size change rate before and after formation of hydrophilic polymer layer (%) | Film thickness dried state of hydrophilic polymer layer (nm) | Film thickness frozen state of hydrophilic polymer layer (nm) |
| --- | --- | --- | --- | --- | --- |
| Comparative Example 40 | 14.00 | 14.00 | 0.0 | 0 | 0 |
| Comparative Example 41 | 14.20 | 14.10 | −0.7 | 0 | 0 |
| Comparative Example 42 | 14.20 | 14.15 | −0.4 | 0 | 0 |
| Comparative Example 43 | 14.00 | *Impossible to perform coating due to inferior solubility | *Impossible to perform coating due to inferior solubility | *Impossible to perform coating due to inferior solubility | *Impossible to perform coating due to inferior solubility |
| Comparative Example 44 | 14.20 | None | None | 0 | 0 |

The invention claimed is:

1. A method for producing a medical device, which comprises a step of disposing a solution containing a hydrophilic polymer having a hydroxyl group and an amide group and a substrate on or in a support, and heating the solution and the substrate through the support, wherein
a pH of the solution before starting the heating step is in a range of 2.0 or higher and 6.0 or lower, and a pH of the solution after completion of the heating step is in a range of 2.0 or higher and 6.0 or lower.

2. The method for producing a medical device according to claim 1, wherein the hydrophilic polymer is fixed to at least a part of the substrate by the step of heating the solution and the substrate through the support.

3. The method for producing a medical device according to claim 1, wherein the support is a mold used for molding the substrate.

4. The method for producing a medical device according to claim 1, wherein the heating step is performed in an autoclave.

5. The method for producing a medical device according to claim 1, wherein a change rate between the moisture content (% by mass) of the substrate and the moisture content (% by mass) of the resulting medical device is 10 percentage points or less.

6. The method for producing a medical device according to claim 1, wherein a hydrophilic polymer layer is formed on at least a part of a substrate surface by the heating step, and in the hydrophilic polymer layer, the content of the polymer other than the hydrophilic polymer having a hydroxyl group and an amide group is 3 parts by mass or less based on 100 parts by mass of the total amount of the hydrophilic polymer having a hydroxyl group and an amide group.

7. The method for producing a medical device according to claim 1, wherein the medical device is an ophthalmic lens, a dermal covering material, a wound dressing material, a skin protection material, a skin medicine carrier, an infusion tube, a gas delivery tube, a drain tube, a blood circuit, a covering tube, a catheter, a stent, a sheath biosensor chip, or an endoscopic dressing material.

8. The method for producing a medical device according to claim 7, wherein the medical device is an ophthalmic lens.

9. The method for producing a medical device according to claim 8, wherein the ophthalmic lens is a contact lens.

10. The method for producing a medical device according to claim 3, wherein a mold used for molding the substrate is a mold used for molding a contact lens substrate.

11. The method for producing a medical device according to claim 1, wherein the support is a container for the sale of contact lenses.

* * * * *